(12) United States Patent
Yin et al.

(10) Patent No.: US 12,734,066 B2
(45) Date of Patent: Sep. 15, 2026

(54) SYSTEMS, APPARATUS AND METHODS FOR LEAK PREVENTION WITH TARGETED TEMPERATURE MANAGEMENT GEL PADS

(71) Applicant: C. R. Bard, Inc., Franklin Lakes, NJ (US)

(72) Inventors: Zhihui Yin, Lilburn, GA (US); Ping Huang, Covington, GA (US); Hannah Rose Kriscovich, Marietta, GA (US); Patrick Hudson Chancy, Atlanta, GA (US); Kevin A. Luczynski, Atlanta, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 1005 days.

(21) Appl. No.: 17/848,039

(22) Filed: Jun. 23, 2022

(65) Prior Publication Data

US 2023/0011631 A1 Jan. 12, 2023

Related U.S. Application Data

(60) Provisional application No. 63/220,864, filed on Jul. 12, 2021.

(51) Int. Cl.
*A61F 7/08* (2006.01)
*A61F 7/00* (2006.01)

(52) U.S. Cl.
CPC ...... *A61F 7/086* (2013.01); *A61F 2007/0001* (2013.01); *A61F 2007/0054* (2013.01)

(58) Field of Classification Search
CPC ................. A61F 2007/0054; A61F 2007/0056
See application file for complete search history.

(56) References Cited

U.S. PATENT DOCUMENTS 2,167,865 A 8/1939 Beecher
2,250,325 A 7/1941 Barnes
(Continued)

FOREIGN PATENT DOCUMENTS

AU 678753 B3 6/1997
AU 2007201161 B2 12/2010
(Continued)

OTHER PUBLICATIONS

PCT/US2021/065144 filed Dec. 23, 2021 International Search Report dated Oct. 4, 2022.

(Continued)

*Primary Examiner* — Kaitlyn E Smith
(74) *Attorney, Agent, or Firm* — Rutan & Tucker LLP

(57) ABSTRACT

A targeted temperature management (TTM) system is disclosed that includes a TTM module to provide a TTM fluid, a fluid delivery line (FDL) including a FDL hub, a fluid delivery lumen and a fluid return lumen, and a pad to facilitate thermal energy transfer between the TTM fluid and a patient, the pad including a fluid delivery conduit extending away from the pad portion and including a first leak prevention valve configured to enable the TTM fluid to flow in a distal direction while preventing flow in a proximal direction, and a fluid return conduit extending away from the pad portion, the fluid return conduit including (i) a return conduit connector at a proximal end thereof, and (ii) a second leak prevention valve configured to enable the TTM fluid to flow in the proximal direction while preventing flow in the distal direction.

15 Claims, 7 Drawing Sheets

(56) References Cited

U.S. PATENT DOCUMENTS 2,296,207 A 9/1942 Kittinger
2,595,328 A 5/1952 Bowen
2,602,302 A 7/1952 Poux
2,726,658 A 12/1955 Chessey
2,807,809 A 10/1957 Kottemann
3,075,529 A 1/1963 Young, Jr.
3,091,242 A 5/1963 Johnson, Jr. et al.
3,212,286 A 10/1965 Curtis
3,506,013 A 4/1970 Zdenek
3,734,293 A 5/1973 Biskis
3,830,676 A 8/1974 Elkins
3,867,939 A 2/1975 Moore et al.
3,900,035 A 8/1975 Welch et al.
3,927,671 A 12/1975 Chittenden et al.
3,945,617 A 3/1976 Callery
3,995,621 A 12/1976 Fletcher et al.
4,059,293 A 11/1977 Sipler
4,092,982 A 6/1978 Salem
4,108,146 A 8/1978 Golden
4,114,620 A 9/1978 Moore et al.
4,118,946 A 10/1978 Tubin
4,149,541 A 4/1979 Gammons et al.
4,154,245 A 5/1979 Daily
4,161,210 A 7/1979 Reid et al.
4,195,631 A 4/1980 Baucom
4,311,022 A 1/1982 Hall
4,444,727 A 4/1984 Yanagihara et al.
4,508,123 A 4/1985 Wyatt et al.
4,580,408 A 4/1986 Stuebner
4,753,241 A 6/1988 Brannigan et al.
4,834,705 A 5/1989 Vaillancourt
4,846,176 A 7/1989 Golden
4,867,748 A 9/1989 Samuelsen
4,884,304 A 12/1989 Elkins
4,886,063 A 12/1989 Crews
4,908,248 A 3/1990 Nakashima et al.
4,919,134 A 4/1990 Streeter
4,962,761 A 10/1990 Golden
4,971,056 A 11/1990 Seacord
4,981,135 A 1/1991 Hardy
4,989,607 A 2/1991 Keusch et al.
5,000,252 A 3/1991 Faghri
5,005,374 A 4/1991 Spitler
5,050,596 A 9/1991 Walasek et al.
5,062,414 A 11/1991 Grim
5,072,875 A 12/1991 Zacoi
5,090,409 A 2/1992 Genis
5,097,829 A 3/1992 Quisenberry
5,111,668 A 5/1992 Parrish et al.
5,113,666 A 5/1992 Parrish et al.
5,133,348 A 7/1992 Mayn
5,146,625 A 9/1992 Steele et al.
5,154,706 A 10/1992 Cartmell et al.
5,190,032 A 3/1993 Zacoi
5,265,669 A 11/1993 Schneider
5,268,022 A 12/1993 Garrett et al.
5,289,695 A 3/1994 Parrish et al.
5,300,103 A 4/1994 Stempel et al.
5,304,213 A 4/1994 Berke et al.
5,304,216 A 4/1994 Wallace
5,320,164 A 6/1994 Szczesuil et al.
5,329,638 A 7/1994 Hansen et al.
5,383,919 A 1/1995 Kelly et al.
5,393,462 A 2/1995 Avery
5,405,366 A 4/1995 Fox et al.
5,407,421 A 4/1995 Goldsmith
5,409,500 A 4/1995 Dyrek
5,411,541 A 5/1995 Bell et al.
5,423,751 A 6/1995 Harrison et al.
5,431,622 A 7/1995 Pyrozyk et al.
5,437,673 A 8/1995 Baust et al.
5,456,701 A 10/1995 Stout
5,466,250 A 11/1995 Johnson, Jr. et al.
5,470,353 A 11/1995 Jensen
5,476,489 A 12/1995 Koewler
5,484,448 A 1/1996 Steele et al.
5,486,207 A 1/1996 Mahawili
5,514,169 A 5/1996 Dickerhoff et al.
5,545,194 A 8/1996 Augustine
5,566,413 A 10/1996 Webb et al.
5,605,144 A 2/1997 Simmons et al.
5,609,620 A 3/1997 Daily
5,620,482 A 4/1997 Augustine et al.
5,624,477 A 4/1997 Armond
5,634,940 A 6/1997 Panyard
5,640,728 A 6/1997 Graebe
5,645,855 A 7/1997 Lorenz
5,658,325 A 8/1997 Augustine
5,662,695 A 9/1997 Mason et al.
5,683,439 A 11/1997 Jensen
5,720,774 A 2/1998 Glucksman
5,733,318 A 3/1998 Augustine
5,755,755 A 5/1998 Panyard
5,785,716 A 7/1998 Bayron et al.
5,806,335 A 9/1998 Herbert et al.
5,824,025 A 10/1998 Augustine
5,837,002 A 11/1998 Augustine et al.
5,840,080 A 11/1998 Der Ovanesian
5,843,145 A 12/1998 Brink
5,871,526 A 2/1999 Gibbs et al.
5,879,378 A 3/1999 Usui
5,887,437 A 3/1999 Maxim
5,913,849 A 6/1999 Sundstrom et al.
5,947,914 A 9/1999 Augustine
5,948,012 A 9/1999 Mahaffey et al.
5,968,000 A 10/1999 Harrison et al.
5,986,163 A 11/1999 Augustine
5,989,285 A 11/1999 DeVilbiss et al.
6,010,528 A 1/2000 Augustine et al.
6,019,783 A 2/2000 Philips et al.
6,030,412 A 2/2000 Klatz et al.
6,047,106 A 4/2000 Salyer
6,074,415 A 6/2000 Der Ovanesian
6,083,256 A 7/2000 Der Ovanesian
6,083,418 A 7/2000 Czarnecki et al.
6,117,164 A 9/2000 Gildersleeve et al.
6,176,869 B1 1/2001 Mason et al.
6,176,870 B1 1/2001 Augustine
6,185,744 B1 2/2001 Poholski
6,188,930 B1 2/2001 Carson
6,189,149 B1 2/2001 Allen
6,189,550 B1 2/2001 Stickel et al.
6,197,045 B1 3/2001 Carson
6,234,538 B1 5/2001 Lauer
6,238,427 B1 5/2001 Matta
6,255,552 B1 7/2001 Cummings et al.
6,257,011 B1 7/2001 Siman-Tov et al.
6,290,716 B1 9/2001 Augustine
6,336,935 B1 1/2002 Davis et al.
6,349,560 B1 2/2002 Maier-Laxhuber et al.
6,352,550 B1 3/2002 Gildersleeve et al.
6,364,937 B1 4/2002 McMahon
6,371,976 B1 4/2002 Vrzalik et al.
6,375,674 B1 4/2002 Carson
6,389,839 B1 5/2002 Sabin
6,436,130 B1 8/2002 Philips et al.
6,451,036 B1 9/2002 Heitzmann et al.
6,454,792 B1 9/2002 Noda et al.
6,461,379 B1 10/2002 Carson et al.
6,463,212 B1 10/2002 Salyer
6,503,297 B1 1/2003 Lu et al.
6,508,831 B1 1/2003 Kushnir
6,508,859 B1 1/2003 Zia et al.
6,511,501 B1 1/2003 Augustine et al.
6,511,502 B2 1/2003 Fletcher
6,517,510 B1 2/2003 Stewart et al.
D471,987 S 3/2003 Hoglund et al.
D472,322 S 3/2003 Hoglund et al.
6,551,348 B1 4/2003 Blalock et al.
D474,544 S 5/2003 Hoglund et al.
6,559,096 B1 5/2003 Smith et al.
6,584,797 B1 7/2003 Smith et al.
6,589,270 B2 7/2003 Augustine
6,591,630 B2 7/2003 Smith et al.

(56) References Cited

U.S. PATENT DOCUMENTS 6,601,404 B1 8/2003 Roderick
6,613,030 B1 9/2003 Coles et al.
6,620,187 B2 9/2003 Carson et al.
6,620,188 B1 9/2003 Ginsburg et al.
6,645,232 B2 11/2003 Carson
6,648,905 B2 11/2003 Hoglund et al.
6,653,607 B2 11/2003 Ellis et al.
D483,125 S 12/2003 Hoglund et al.
6,660,027 B2 12/2003 Gruszecki et al.
6,669,715 B2 12/2003 Hoglund et al.
6,682,525 B2 1/2004 Lalonde et al.
D487,147 S 2/2004 Ellingboe et al.
D487,148 S 2/2004 Ellingboe et al.
6,688,132 B2 2/2004 Smith et al.
6,692,518 B2 2/2004 Carson
6,699,267 B2 3/2004 Voorhees et al.
6,701,724 B2 3/2004 Smith et al.
6,743,250 B2 6/2004 Renfro
6,755,801 B2 6/2004 Utterberg et al.
6,755,852 B2 6/2004 Lachenbruch et al.
D492,773 S 7/2004 Ellingboe et al.
6,770,848 B2 8/2004 Haas et al.
6,799,063 B2 9/2004 Carson
6,800,087 B2 10/2004 Papay et al.
6,802,855 B2 10/2004 Ellingboe et al.
6,802,885 B2 10/2004 Luk et al.
6,818,012 B2 11/2004 Ellingboe
6,827,728 B2 12/2004 Ellingboe et al.
6,846,322 B2 1/2005 Kane et al.
6,858,068 B2 2/2005 Smith et al.
6,878,156 B1 4/2005 Noda
6,893,453 B2 5/2005 Agarwal et al.
6,904,956 B2 6/2005 Noel
6,909,074 B1 6/2005 Bradley
6,921,198 B2 7/2005 Gruszecki et al.
6,931,875 B1 8/2005 Allen et al.
6,942,644 B2 9/2005 Worthen
6,960,243 B1 11/2005 Smith et al.
6,968,711 B2 11/2005 Smith et al.
6,969,399 B2 11/2005 Schock et al.
7,008,445 B2 3/2006 Lennox
7,022,099 B2 4/2006 Litzie et al.
7,044,960 B2 5/2006 Voorhees et al.
7,052,509 B2 5/2006 Lennox et al.
7,055,575 B2 6/2006 Noel
7,056,335 B2 6/2006 Agarwal et al.
7,063,718 B2 6/2006 Dobak, III
7,077,858 B2 7/2006 Fletcher et al.
7,097,657 B2 8/2006 Noda et al.
7,101,389 B1 9/2006 Augustine et al.
7,122,047 B2 10/2006 Grahn et al.
7,160,316 B2 1/2007 Hamilton et al.
7,172,586 B1 2/2007 Dae et al.
7,240,720 B2 7/2007 Noel
7,303,554 B2 12/2007 Lalonde et al.
7,303,579 B2 12/2007 Schock et al.
7,338,516 B2 3/2008 Quincy, III et al.
7,361,186 B2 4/2008 Voorhees et al.
7,377,935 B2 5/2008 Schock et al.
7,507,250 B2 3/2009 Lennox
7,517,360 B2 4/2009 Frey et al.
RE40,815 E 6/2009 Kudaravalli et al.
7,547,320 B2 6/2009 Schook et al.
RE40,868 E 8/2009 Ryba et al.
7,621,944 B2 11/2009 Wilson et al.
7,621,945 B2 11/2009 Lennox et al.
7,666,213 B2 2/2010 Freedman, Jr. et al.
7,678,716 B2 3/2010 Yahiaoui et al.
7,686,840 B2 3/2010 Quincy, III et al.
7,727,228 B2 6/2010 Abboud et al.
7,731,739 B2 6/2010 Schock et al.
7,744,640 B1 6/2010 Faries, Jr. et al.
7,749,261 B2 7/2010 Hansen et al.
7,763,061 B2 7/2010 Schorr et al.
7,771,461 B2 8/2010 Schock et al.
7,784,304 B2 8/2010 Trinh et al.
7,799,063 B2 9/2010 Ingram et al.
7,827,815 B2 11/2010 Carson et al.
7,867,266 B2 1/2011 Collins
7,892,269 B2 2/2011 Collins et al.
7,896,910 B2 3/2011 Schirrmacher et al.
7,918,243 B2 4/2011 Diodati et al.
8,047,010 B2 11/2011 Carson et al.
8,052,624 B2 11/2011 Buchanan et al.
8,066,752 B2 11/2011 Hamilton et al.
8,182,521 B2 5/2012 Kane et al.
8,187,697 B2 5/2012 Quincy, III et al.
8,216,163 B2 7/2012 Edelman
8,283,602 B2 10/2012 Augustine et al.
8,454,671 B2 6/2013 Lennox et al.
D685,916 S 7/2013 Hoglund
8,491,644 B1 7/2013 Carson et al.
8,597,217 B2 12/2013 Lowe et al.
8,597,339 B2 12/2013 Augustine et al.
8,603,150 B2 12/2013 Kane et al.
8,632,576 B2 1/2014 Quisenberry
8,647,374 B2 2/2014 Koewler
8,715,330 B2 5/2014 Lowe et al.
8,778,119 B2 7/2014 Starr et al.
8,808,344 B2 8/2014 Scott et al.
8,840,581 B2 9/2014 McGill et al.
9,034,458 B2 5/2015 Li
9,078,742 B2 7/2015 Quincy, III et al.
9,089,462 B1 7/2015 Lafleche
9,211,358 B2 12/2015 Sinko et al.
9,278,024 B2 3/2016 Scott et al.
9,333,112 B2 5/2016 Carson
9,433,527 B2 9/2016 Varga et al.
9,552,706 B2 1/2017 Schneider, II et al.
9,566,185 B2 2/2017 Carson et al.
9,622,907 B2 4/2017 Carson et al.
9,642,404 B2 5/2017 Giles et al.
9,687,386 B2 6/2017 Carson
9,763,823 B2 9/2017 Voorhees et al.
9,907,889 B2 3/2018 Locke et al.
10,010,452 B2 7/2018 Wenske et al.
10,123,902 B2 11/2018 Carson et al.
10,220,198 B2 3/2019 Fuchs et al.
10,258,501 B2 4/2019 Carson
10,376,412 B2 8/2019 Brienza et al.
10,441,458 B2 10/2019 Voorhees et al.
10,441,707 B2 10/2019 Voorhees et al.
10,548,778 B2 2/2020 Hassenpflug et al.
10,610,424 B1 4/2020 Hoover
D887,426 S 6/2020 Matsushita
10,912,672 B1 2/2021 Jones et al.
D922,424 S 6/2021 Frueh et al.
D925,574 S 7/2021 Beko
D928,188 S 8/2021 Giannino et al.
11,173,071 B1 11/2021 Tawil et al.
D939,550 S 12/2021 Miyai et al.
11,234,859 B2 2/2022 Voorhees et al.
D947,216 S 3/2022 Leininger
11,285,039 B2 3/2022 Steele et al.
D948,534 S 4/2022 Bessette et al.
D952,666 S 5/2022 Sajan
D959,475 S 8/2022 Norman
D960,191 S 8/2022 Feit et al.
D973,067 S 12/2022 Oh et al.
11,975,123 B2 5/2024 Appel et al.
2001/0034545 A1 10/2001 Elkins
2001/0039439 A1 11/2001 Elkins et al.
2002/0007203 A1 1/2002 Gilmartin et al.
2002/0015689 A1 2/2002 Munro et al.
2002/0107558 A1 8/2002 Clifton et al.
2002/0111657 A1 8/2002 Dae et al.
2002/0138121 A1 9/2002 Fox
2002/0161419 A1 10/2002 Carson et al.
2003/0074038 A1 4/2003 Gruszecki et al.
2003/0078638 A1 4/2003 Voorhees et al.
2003/0078639 A1 4/2003 Carson
2003/0078640 A1 4/2003 Carson et al.
2003/0109911 A1 6/2003 Lachenbruch et al.
2003/0114903 A1 6/2003 Ellingboe

(56) References Cited

U.S. PATENT DOCUMENTS

2003/0135252 A1 7/2003 MacHold et al.
2003/0149359 A1 8/2003 Smith
2003/0149461 A1 8/2003 Johnson
2003/0150232 A1 8/2003 Brudnicki
2003/0163179 A1 8/2003 Hoglund et al.
2003/0163180 A1 8/2003 Hoglund et al.
2003/0163183 A1 8/2003 Carson
2003/0163185 A1 8/2003 Carson
2003/0212416 A1 11/2003 Cinelli et al.
2004/0030372 A1 2/2004 Ellingboe et al.
2004/0030373 A1 2/2004 Ellingboe et al.
2004/0059212 A1 3/2004 Abreu
2004/0064170 A1 4/2004 Radons et al.
2004/0064171 A1 4/2004 Briscoe et al.
2004/0073280 A1 4/2004 Dae et al.
2004/0082886 A1 4/2004 Timpson
2004/0087606 A1 5/2004 Voorhees et al.
2004/0133253 A1 7/2004 Grahn et al.
2004/0158303 A1 8/2004 Lennox et al.
2004/0225341 A1 11/2004 Schock et al.
2004/0243122 A1 12/2004 Auth et al.
2004/0252750 A1 12/2004 Gruszecki et al.
2004/0255362 A1 12/2004 Soerens et al.
2004/0260369 A1 12/2004 Schock et al.
2004/0267339 A1 12/2004 Yon et al.
2005/0028551 A1 2/2005 Noda et al.
2005/0060012 A1 3/2005 Voorhees et al.
2005/0065583 A1 3/2005 Voorhees et al.
2005/0096714 A1 5/2005 Freedman et al.
2005/0177212 A1 8/2005 Njemanze
2005/0187502 A1 8/2005 Krempel et al.
2005/0244629 A1 11/2005 Usui et al.
2005/0288749 A1 12/2005 Lachenbruch
2006/0024053 A1 2/2006 Grant
2006/0030916 A1 2/2006 Lennox
2006/0036304 A1 2/2006 Cordani et al.
2006/0058858 A1 3/2006 Smith
2006/0069418 A1 3/2006 Schock et al.
2006/0074469 A1* 4/2006 Lennox ................ A61F 7/0085
607/110
2006/0122673 A1 6/2006 Callister et al.
2006/0124141 A1 6/2006 Dobak
2006/0136023 A1 6/2006 Dobak
2006/0161232 A1 7/2006 Kasza et al.
2006/0190066 A1 8/2006 Worthen
2006/0235114 A1 10/2006 Kitazono et al.
2006/0247744 A1 11/2006 Nest et al.
2006/0276089 A1 12/2006 Amarasinghe et al.
2006/0287697 A1 12/2006 Lennox
2006/0293734 A1 12/2006 Scott et al.
2007/0016270 A1 1/2007 Stelea et al.
2007/0043409 A1 2/2007 Brian et al.
2007/0049997 A1 3/2007 Fields et al.
2007/0054122 A1 3/2007 Paisner et al.
2007/0068931 A1 3/2007 Augustine et al.
2007/0073368 A1 3/2007 Cazzini et al.
2007/0100404 A1 5/2007 Ko et al.
2007/0173735 A1 7/2007 Callister et al.
2007/0213793 A1 9/2007 Hayes
2007/0225782 A1 9/2007 Taylor
2007/0244475 A1 10/2007 Carson et al.
2007/0270925 A1 11/2007 Levinson
2008/0027523 A1 1/2008 Behringer et al.
2008/0046046 A1 2/2008 Ginsburg
2008/0114431 A1 5/2008 Ginsburg
2008/0147152 A1 6/2008 Quincy et al.
2008/0249524 A1 10/2008 Dunning
2008/0255644 A1 10/2008 Carson
2008/0269852 A1 10/2008 Lennox et al.
2008/0275534 A1 11/2008 Noel
2009/0018504 A1 1/2009 Pile-Spellman et al.
2009/0043366 A1 2/2009 Dae
2009/0066079 A1 3/2009 Miros et al.
2009/0088825 A1 4/2009 Ota
2009/0099629 A1 4/2009 Carson et al.
2009/0131835 A1 5/2009 Voorhees et al.
2009/0149925 A1 6/2009 MacDonald et al.
2009/0157000 A1 6/2009 Waller
2009/0177184 A1 7/2009 Christensen et al.
2009/0182400 A1 7/2009 Dae et al.
2009/0228082 A1 9/2009 Ross, III et al.
2009/0250367 A1 10/2009 Murdoch et al.
2009/0280182 A1 11/2009 Beck et al.
2009/0287283 A1 11/2009 Biser et al.
2009/0299287 A1 12/2009 Carson et al.
2009/0312823 A1 12/2009 Patience et al.
2009/0326619 A1 12/2009 Kagan
2010/0016933 A1 1/2010 Chen et al.
2010/0137951 A1 6/2010 Lennox et al.
2010/0168825 A1 7/2010 Barbknecht
2010/0198122 A1 8/2010 Freund
2010/0198320 A1 8/2010 Pierre et al.
2010/0204765 A1 8/2010 Hall et al.
2010/0217260 A1 8/2010 Aramayo
2010/0241073 A1 9/2010 Andersen et al.
2010/0312160 A1 12/2010 Creighton et al.
2010/0312202 A1 12/2010 Henley et al.
2011/0021960 A1 1/2011 Filtvedt et al.
2011/0029051 A1 2/2011 Ross
2011/0045056 A1 2/2011 Munro et al.
2011/0125238 A1 5/2011 Nofzinger
2011/0152982 A1 6/2011 Richardson
2011/0166633 A1 7/2011 Stull
2011/0172749 A1 7/2011 Christensen et al.
2011/0172750 A1 7/2011 Cassidy et al.
2011/0306972 A1 12/2011 Widenhouse et al.
2011/0307040 A1 12/2011 Peterson
2011/0308781 A1 12/2011 O'Riordan et al.
2011/0313497 A1 12/2011 Mcfarlane
2012/0046720 A1 2/2012 Ishizaki
2012/0065715 A1 3/2012 Carson
2012/0080031 A1 4/2012 Belson
2012/0095536 A1 4/2012 Machold et al.
2012/0172774 A1 7/2012 Lowe et al.
2012/0185021 A1 7/2012 Johnson et al.
2012/0191035 A1 7/2012 Stephan
2012/0204881 A1 8/2012 Davidson et al.
2012/0220960 A1 8/2012 Ruland
2012/0288848 A1 11/2012 Latham et al.
2013/0023808 A1 1/2013 Brown et al.
2013/0116760 A1 5/2013 Carson et al.
2013/0138185 A1 5/2013 Paxman et al.
2013/0190667 A1 7/2013 Kane et al.
2013/0238042 A1 9/2013 Gildersleeve et al.
2013/0238043 A1 9/2013 Beardall et al.
2013/0310725 A1 11/2013 Jerrells et al.
2014/0039451 A1 2/2014 Bangera et al.
2014/0046411 A1 2/2014 Elkins et al.
2014/0172050 A1 6/2014 Dabrowiak
2014/0214138 A1 7/2014 Voorhees et al.
2014/0222121 A1 8/2014 Spence et al.
2014/0228717 A1 8/2014 Parish et al.
2014/0228918 A1 8/2014 Brienza et al.
2014/0276253 A1 9/2014 Varga et al.
2014/0277301 A1 9/2014 Varga et al.
2014/0288621 A1 9/2014 Efremkin
2014/0316494 A1 10/2014 Augustine et al.
2014/0343639 A1 11/2014 Hopper et al.
2015/0025606 A1 1/2015 Davis
2015/0051673 A1 2/2015 Rivas Tapia
2015/0119963 A1 4/2015 Cosse
2015/0173942 A1 6/2015 Whitely
2015/0209174 A1 7/2015 Abreu
2015/0209192 A1 7/2015 Manion et al.
2015/0223972 A1 8/2015 Dabrowiak
2015/0230973 A1 8/2015 Dabrowiak et al.
2015/0231009 A1 8/2015 Lewis
2015/0250643 A1 9/2015 Paradis
2015/0290042 A1 10/2015 Freer et al.
2015/0366703 A1 12/2015 Du
2015/0373781 A1 12/2015 Augustine et al.
2015/0374045 A1 12/2015 Codner et al.
2016/0008166 A1 1/2016 Voorhees et al.
2016/0022477 A1 1/2016 Schaefer et al.

(56) References Cited

U.S. PATENT DOCUMENTS

2016/0038336 A1 2/2016 Hilton et al.
2016/0310316 A1 10/2016 Hixson, Jr.
2016/0324683 A1 11/2016 Carson
2017/0049618 A1 2/2017 Ward et al.
2017/0135855 A1 5/2017 Stefan et al.
2017/0151087 A1 6/2017 Carson et al.
2017/0189225 A1 7/2017 Voorhees et al.
2017/0209305 A1 7/2017 Kaforey et al.
2017/0224528 A1 8/2017 Berg et al.
2017/0246029 A1 8/2017 Clark
2017/0246031 A1 8/2017 Benyaminpour et al.
2017/0246374 A1 8/2017 Voorhees et al.
2017/0348144 A1 12/2017 Taylor et al.
2017/0348145 A1 12/2017 Voorhees et al.
2017/0354534 A1 12/2017 Paradis et al.
2018/0000255 A1 1/2018 Youngblood et al.
2018/0014967 A1 1/2018 Taylor
2018/0042762 A1 2/2018 Galer
2018/0042763 A1 2/2018 Galer et al.
2018/0064594 A1 3/2018 Finch, Jr. et al.
2018/0140407 A1 5/2018 Yoskowitz
2018/0207024 A1 7/2018 Dabrowiak et al.
2018/0214297 A1 8/2018 Hughett et al.
2018/0214302 A1 8/2018 Dabrowiak et al.
2018/0263677 A1 9/2018 Hilton et al.
2018/0263748 A1 9/2018 Quinn
2018/0295980 A1 10/2018 Boersma et al.
2018/0376539 A1 12/2018 Augustine et al.
2019/0083322 A1 3/2019 Huang et al.
2019/0085644 A1 3/2019 Ames et al.
2019/0099288 A1 4/2019 Vergara et al.
2019/0117446 A1 4/2019 Carson et al.
2019/0192337 A1 6/2019 Taylor et al.
2019/0201574 A1 7/2019 Delury et al.
2019/0262169 A1 8/2019 Vergara et al.
2019/0331277 A1 10/2019 Vachon
2020/0001022 A1 1/2020 Landy, III et al.
2020/0071051 A1 3/2020 Lewis
2020/0129326 A1 4/2020 Sinha et al.
2020/0155341 A1 5/2020 Voorhees et al.
2020/0214471 A1 7/2020 Paperno
2020/0246180 A1 8/2020 Liang et al.
2020/0345971 A1 11/2020 Schirm et al.
2020/0405530 A1 12/2020 Taylor et al.
2021/0060230 A1 3/2021 Hopper et al.
2021/0123641 A1 4/2021 Monazami et al.
2022/0087874 A1 3/2022 Schneider et al.
2022/0151821 A1 5/2022 Voorhees et al.
2022/0192865 A1 6/2022 Hughett, Sr. et al.
2022/0192867 A1 6/2022 Stich et al.
2022/0233344 A1 7/2022 Hoglund
2022/0233347 A1 7/2022 Canary et al.
2022/0265468 A1 8/2022 Xu et al.
2022/0280336 A1 9/2022 Smith et al.
2022/0287875 A1 9/2022 Minchew et al.
2022/0287876 A1 9/2022 Smith et al.
2022/0296413 A1 9/2022 Jones
2022/0296414 A1 9/2022 Bible et al.
2022/0304847 A1 9/2022 Kuroda et al.
2022/0313478 A1 10/2022 Johnston
2022/0347009 A1 11/2022 Hughett, Sr. et al.
2022/0401259 A1 12/2022 Basciano et al.
2022/0406017 A1 12/2022 Wang et al.
2023/0000668 A1 1/2023 Walker et al.
2023/0009524 A1 1/2023 Johnston et al.
2023/0019048 A1 1/2023 Stich et al.
2023/0021245 A1 1/2023 Walker et al.
2023/0040583 A1 2/2023 Falis et al.
2023/0077318 A9 3/2023 Voorhees et al.
2023/0190519 A1 6/2023 Stich et al.
2024/0065884 A1 2/2024 Fallows et al.
2024/0082052 A1 3/2024 Cho et al.
2024/0091054 A1 3/2024 Boone-Worthman et al.
2024/0099878 A1 3/2024 Voorhees et al.
2024/0108497 A1 4/2024 Daw et al.
2024/0366422 A1 11/2024 Johnston et al.
2025/0032310 A1 1/2025 Stich et al.
2025/0041107 A1 2/2025 Walker et al.
2025/0110628 A1 4/2025 Litman et al.
2025/0134705 A1 5/2025 Stich et al.
2025/0143918 A1 5/2025 Voorhees et al.
2025/0161107 A1 5/2025 Stich et al.
2025/0198550 A1 6/2025 Johnston et al.
2025/0332025 A1 10/2025 Brooks et al.
2026/0026965 A1 1/2026 Xu et al.
2026/0102279 A1 4/2026 Canary et al.

FOREIGN PATENT DOCUMENTS

CA 2729122 A1 7/2002
CA 2193385 C 9/2006
CN 102026596 A 4/2011
CN 101389372 B 8/2012
CN 102746518 A 10/2012
CN 103939695 B 3/2016
CN 305928532 7/2020
CN 111643265 A 9/2020
CN 306402573 3/2021
CN 113230017 A 8/2021
CN 307690236 11/2022
CN 309180016 3/2025
DE 102014118510 A1 6/2016
EP 0862901 A1 9/1998
EP 1073388 A1 2/2001
EP 1616543 A2 1/2006
EP 1641503 A2 4/2006
EP 1718894 B1 7/2010
EP 2204150 A1 7/2010
EP 2269546 A1 1/2011
GB 2118440 A 11/1983
JP H09508045 A 8/1997
JP 2002-534160 A 10/2002
JP 2007029638 A 2/2007
JP 2013248293 A 12/2013
KR 20110020420 A 3/2011
WO 9807397 A1 2/1998
WO 98/31310 A1 7/1998
WO 199944552 A1 9/1999
WO 9953874 A1 10/1999
WO 2000040185 A1 7/2000
WO 2003086253 A2 10/2003
WO 2004075949 A2 9/2004
WO 2005028984 A1 3/2005
WO 2005117546 A2 12/2005
WO 2007120677 A2 10/2007
WO 2009/090403 A1 7/2009
WO 2009147413 A1 12/2009
WO 2009148636 A1 12/2009
WO 2012125916 A2 9/2012
WO 2012138980 A2 10/2012
WO 2015084925 A1 6/2015
WO 2016057119 A1 4/2016
WO 2016123500 A1 8/2016
WO 2017/127768 A1 7/2017
WO 2018075576 A1 4/2018
WO 2022/159879 A1 7/2022
WO 2022155130 A1 7/2022
WO 2022155132 A1 7/2022
WO 2022159513 A1 7/2022
WO 2022/165068 A1 8/2022
WO 2022235513 A1 11/2022
WO 2023121674 A1 6/2023
WO 2023140870 A1 7/2023
WO 2023154050 A1 8/2023
WO 2023229609 A1 11/2023

OTHER PUBLICATIONS

PCT/US2022/026999 filed Apr. 29, 2022 International Search Report and Written Opinion dated Oct. 24, 2022.

U.S. Appl. No. 17/848,074, filed Jun. 23, 2022 Advisory Action dated Jul. 9, 2024.

(56) References Cited

OTHER PUBLICATIONS

U.S. Appl. No. 17/848,074, filed Jun. 23, 2022 Final Office Action dated Apr. 26, 2024.
U.S. Appl. No. 17/848,074, filed Jun. 23, 2022 Non-Final Office Action dated Nov. 30, 2023.
U.S. Appl. No. 18/536,087, filed Dec. 11, 2023 Non-Final Office Action dated Jun. 28, 2024.
PCT/US2022/011980 filed Jan. 11, 2022 International Search Report and Written Opinion dated Apr. 13, 2022.
PCT/US2022/013007 filed Jan. 19, 2022 International Search Report and Written Opinion dated Apr. 22, 2022.
PCTUS2022011971 filed Jan. 11, 2022 International Search Report and Written Opinion dated Apr. 21, 2022.
U.S. Appl. No. 17/589,849, filed Jan. 31, 2022 Final Office Action dated Jun. 27, 2023.
U.S. Appl. No. 17/589,849, filed Jan. 31, 2022 Non-Final Office Action dated Apr. 12, 2023.
U.S. Appl. No. 17/589,849, filed Jan. 31, 2022 Notice of Allowance dated Aug. 23, 2023.
Advantage Engineering, "Proper Use of Inhibited Propylene Glycol", Jun. 12, 2001, http://www.ttequip.com/knowledgelibrary/Proper%20Use%20Of%20Inh- ibited%20Propylene%20Glycol.pdf Jun. 12, 2001.
Hyperphysicis, "Thermal Conductivity", available Jul. 31, 2010, https://web.archive.org/web/20100731025127/http://hyperphysics.phy-astr.g- us.edu/hbase/tables.thron.html Jul. 31, 2010.
Murray, R. Z., et al. "Development and use of biomaterials as wound healing therapies" Burns & Trauma (2019) 7:2 https://doi.org/10.1186/s41038-018-0139-7 (2019).
PCT/US2015/045548 filed Aug. 17, 2015 International Search Report and Written Opinion dated Nov. 24, 2015.
Sevgi, M., et al. "Topical Antimicrobials for Burn Infections—An Update" Recent Pat Antiinfect Drug Discov. Dec. 2013 ; 8(3): 161-197.
Stoica, A. E., et al. "Hydrogel Dressings for the Treatment of Burn Wounds: An Up-To-Date Overview" Materials 2020, 13, 2853; doi:10.3390/ma13122853. (2020).
U.S. Appl. No. 15/512,025, filed Mar. 16, 2017 Final Office Action dated Jun. 25, 2020.
U.S. Appl. No. 15/512,025, filed Mar. 16, 2017 Non-Final Office Action dated Jul. 18, 2019.
U.S. Appl. No. 16/597,393, filed Oct. 9, 2019 Corrected Notice of Allowability dated Nov. 18, 2021.
U.S. Appl. No. 16/597,393, filed Oct. 9, 2019 Non-Final Office Action dated Apr. 28, 2021
PCT/US2016/015688 filed Jan. 29, 2016 International Search Report and Written Opinion dated Apr. 1, 2016.
PCT/US2022/013672 filed Jan. 25, 2022, International Search Report and Written Opinion dated Jul. 15, 2022.
PCT/US2022/014147 filed Jan. 27, 2022 International Search Report and Written Opinion dated Jul. 18, 2022.
PCT/US2022/031428 filed May 27, 2022 International Search Report and Written Opinion dated Jan. 30, 2023.
U.S. Appl. No. 17/547,128, filed Dec. 9, 2021 Non-Final Office Action dated Feb. 10, 2025.
U.S. Appl. No. 17/552,309, filed Dec. 15, 2021 Non-Final Office Action dated Mar. 14, 2025.
U.S. Appl. No. 17/552,309, filed Dec. 15, 2021 Restriction Requirement dated Dec. 12, 2024.
U.S. Appl. No. 17/583,090, filed Jan. 24, 2022 Non-Final Office Action dated Feb. 13, 2025.
U.S. Appl. No. 17/584,101, filed Jan. 25, 2022 Non-Final Office Action dated Feb. 5, 2025.
U.S. Appl. No. 17/584,101, filed Jan. 25, 2022 Restriction Requirement dated Nov. 5, 2024.
U.S. Appl. No. 17/678,965, filed Feb. 23, 2022 Non-Final Office Action dated Feb. 12, 2025.
U.S. Appl. No. 17/686,301, filed Mar. 3, 2022 Advisory Action dated Apr. 4, 2025.
U.S. Appl. No. 17/686,301, filed Mar. 3, 2022 Final Office Action dated Jan. 29, 2025.
U.S. Appl. No. 17/689,791, filed Mar. 8, 2022 Non-Final Office Action dated Dec. 30, 2024.
U.S. Appl. No. 17/690,908, filed Mar. 9, 2022 Non-Final Office Action dated Dec. 18, 2024.
U.S. Appl. No. 17/691,990, filed Mar. 10, 2022 Non-Final Office Action dated Dec. 17, 2024.
U.S. Appl. No. 17/694,416, filed Mar. 14, 2022 Non-Final Office Action dated Jan. 22, 2025.
U.S. Appl. No. 17/694,416, filed Mar. 14, 2022 Restriction Requirement dated Nov. 8, 2024.
U.S. Appl. No. 17/700,216, filed Mar. 21, 2022 Non-Final Office Action dated Feb. 5, 2025.
U.S. Appl. No. 17/709,019, filed Mar. 30, 2022 Non-Final Office Action dated Dec. 31, 2024.
U.S. Appl. No. 17/723,210, filed Apr. 18, 2022 Non-Final Office Action dated Dec. 20, 2024.
U.S. Appl. No. 17/848,074, filed Jun. 23, 2022 Notice of Allowance dated Nov. 26, 2024.
U.S. Appl. No. 17/849,419, filed Jun. 24, 2022 Final Office Action dated Feb. 14, 2025.
U.S. Appl. No. 17/849,419, filed Jun. 24, 2022 Non-Final Office Action dated Nov. 8, 2024.
U.S. Appl. No. 17/857,997, filed Jul. 5, 2022 Restriction Requirement dated Feb. 12, 2025.
U.S. Appl. No. 17/859,995, filed Jul. 7, 2022 Non-Final Office Action dated Mar. 11, 2025.
U.S. Appl. No. 17/881,270, filed Aug. 4, 2022 Restriction Requirement dated Feb. 11, 2025.
PCT/US2022/013569 filed Jan. 24, 2022 International Search Report and Written Opinion dated Aug. 29, 2022.
PCT/US2022/016020 filed Feb. 10, 2022 International Search Report and Written Opinion dated Oct. 31, 2022.
U.S. Appl. No. 17/547,128, filed Dec. 9, 2021 Restriction Requirement dated Sep. 5, 2024.
U.S. Appl. No. 17/583,090, filed Jan. 24, 2022 Restriction Requirement dated Sep. 6, 2024.
U.S. Appl. No. 17/686,301, filed Mar. 3, 2022 Non-Final Office Action dated Oct. 1, 2024.
U.S. Appl. No. 17/689,791, filed Mar. 8, 2022 Restriction Requirement dated Oct. 16, 2024.
U.S. Appl. No. 17/691,990, filed Mar. 10, 2022 Restriction Requirement dated Oct. 16, 2024.
U.S. Appl. No. 17/709,019, filed Mar. 30, 2022 Restriction Requirement dated Oct. 16, 2024.
U.S. Appl. No. 17/723,210, filed Apr. 18, 2022 Restriction Requirement dated Oct. 16, 2024.
U.S. Appl. No. 17/848,074, filed Jun. 23, 2022 Non-Final Office Action dated Aug. 15, 2024.
U.S. Appl. No. 18/536,087, filed Dec. 11, 2023 Notice of Allowance dated Aug. 29, 2024.
All in 1: Injection Tracker, posted date unavailable [online], [retrieved Apr. 10, 2025]. Retrieved from internet, https://apps.apple.com/us/app/all-in-1-injection-tracker/id1667540577. (Year: 2025).
Creating an accessible, usable and compelling Injection Site Tracking feature that can used by all our users, posted date May 2020 [u online], [retrieved Apr. 10, 2025]. Retrieved from internet, https://www.bradstricker.com/case-studies/injection-site-tracking. (Year: 2020).
Injection Tracker App, posted date unavailable [online], [retrieved Apr. 10, 2025]. Retrieved from internet, https://www.vladcristei.com/project_page_it. (Year: 2025).
U.S. Appl. No. 17/583,090, filed Jan. 24, 2022 Final Office Action dated Jul. 1, 2025.
U.S. Appl. No. 17/678,965, filed Feb. 23, 2022 Notice of Allowance dated Jun. 3, 2025.
U.S. Appl. No. 17/686,301, filed Mar. 3, 2022 Non-Final Office Action dated May 14, 2025.
U.S. Appl. No. 17/689,791, filed Mar. 8, 2022 Final Office Action dated May 21, 2025.
U.S. Appl. No. 17/690,908, filed Mar. 9, 2022 Final Office Action dated Jun. 24, 2025.

(56) References Cited

OTHER PUBLICATIONS

U.S. Appl. No. 17/694,416, filed Mar. 14, 2022 Final Office Action dated Jun. 20, 2025.
U.S. Appl. No. 17/700,216, filed Mar. 21, 2022 Final Office Action dated Jun. 23, 2025.
U.S. Appl. No. 17/709,019, filed Mar. 30, 2022 Final Office Action dated Jun. 15, 2025.
U.S. Appl. No. 17/723,210, filed Apr. 18, 2022 Final Office Action dated May 21, 2025.
U.S. Appl. No. 17/849,419, filed Jun. 24, 2022 Non-Final Office Action dated Jun. 13, 2025.
U.S. Appl. No. 17/857,997, filed Jul. 5, 2022 Non-Final Office Action dated Apr. 28, 2025.
U.S. Appl. No. 17/881,270, filed Aug. 4, 2022 Non-Final Office Action dated Apr. 28, 2025.
U.S. Appl. No. 18/085,566, filed Dec. 20, 2022 Restriction Requirement dated May 16, 2025.
U.S. Appl. No. 29/939,277, filed Apr. 25, 2024 Non-Final Office Action dated May 13, 2025.
Wound care app can help determine appropriate wounddressings, posted date Apr. 24, 2013 [online], [retrieved Apr. 10, 2025]. Retrieved from internet, https://www.imedicalapps.com/2013/04/wound-care-app-dressings/. (Year: 2013).
U.S. Appl. No. 17/547,128, filed Dec. 9, 2021 Final Office Action dated Aug. 27, 2025.
U.S. Appl. No. 17/552,309, filed Dec. 15, 2021 Advisory Action dated Oct. 2, 2025.
U.S. Appl. No. 17/552,309, filed Dec. 15, 2021 Final Office Action dated Jul. 30, 2025.
U.S. Appl. No. 17/583,090, filed Jan. 24, 2022 Notice of Allowance dated Sep. 30, 2025.
U.S. Appl. No. 17/689,791, filed Mar. 8, 2022 Advisory Action dated Jul. 24, 2025.
U.S. Appl. No. 17/690,908, filed Mar. 9, 2022 Advisory Action dated Sep. 3, 2025.
U.S. Appl. No. 17/690,908, filed Mar. 9, 2022 Non-Final Office Action dated Oct. 2, 2025.
U.S. Appl. No. 17/691,990, filed Mar. 10, 2022 Advisory Action dated Jul. 24, 2025.
U.S. Appl. No. 17/691,990, filed Mar. 10, 2022 Non-Final Office Action dated Aug. 28, 2025.
U.S. Appl. No. 17/694,416, filed Mar. 14, 2022 Advisory Action dated Aug. 20, 2025.
U.S. Appl. No. 17/694,416, filed Mar. 14, 2022 Non-Final Office Action dated Oct. 1, 2025.
U.S. Appl. No. 17/697,879, filed Mar. 17, 2022 Non-Final Office Action dated Sep. 30, 2025.
U.S. Appl. No. 17/700,216, filed Mar. 21, 2022 Advisory Action dated Oct. 9, 2025.
U.S. Appl. No. 17/709,019, filed Mar. 30, 2022 Advisory Action dated Jul. 24, 2025.
U.S. Appl. No. 17/723,210, filed Apr. 18, 2022 Advisory Action dated Jul. 31, 2025.
U.S. Appl. No. 17/859,995, filed Jul. 7, 2022 Final Office Action dated Aug. 22, 2025.
U.S. Appl. No. 18/085,566, filed Dec. 20, 2022 Non-Final Office Action dated Oct. 1, 2025.
U.S. Appl. No. 18/272,026, filed Jul. 12, 2023 Non-Final Office Action dated Jul. 31, 2025.
U.S. Appl. No. 18/274,156, filed Jul. 25, 2023 Non-Final Office Action dated Oct. 1, 2025.
U.S. Appl. No. 18/274,436, filed Jul. 26, 2023 Non-Final Office Action dated Oct. 1, 2025.
U.S. Appl. No. 29/939,277, filed Apr. 25, 2024 Restriction Requirement dated Oct. 2, 2025.
Lustig et al. "Solute Diffusion in Swollen Membranes. IX. Scaling Laws for Solute Diffusion in Gels", Journal of Applied Polymer Science, vol. 36, pp. 735-747 (Year: 1988).
U.S. Appl. No. 17/547,128, filed Dec. 9, 2021 Advisory Action dated Nov. 19, 2025.
U.S. Appl. No. 17/547,128, filed Dec. 9, 2021 Non-Final Office Action dated Dec. 29, 2025.
U.S. Appl. No. 17/552,309, filed Dec. 15, 2021 Non-Final Office Action dated Nov. 5, 2025.
U.S. Appl. No. 17/584,101, filed Jan. 25, 2022 Final Office Action dated Oct. 23, 2025.
U.S. Appl. No. 17/686,301, filed Mar. 3, 2022 Final Office Action dated Oct. 28, 2025.
U.S. Appl. No. 17/689,791, filed Mar. 8, 2022 Non-Final Office Action dated Nov. 5, 2025.
U.S. Appl. No. 17/700,216, filed Mar. 21, 2022 Non-Final Office Action dated Dec. 3, 2025.
U.S. Appl. No. 17/709,019, filed Mar. 30, 2022 Non-Final Office Action dated Nov. 19, 2025.
U.S. Appl. No. 17/723,210, filed Apr. 18, 2022 Non-Final Office Action dated Dec. 29, 2025.
U.S. Appl. No. 17/837,956, filed Jun. 10, 2022 Non-Final Office Action dated Nov. 3, 2025.
U.S. Appl. No. 17/857,997, filed Jul. 5, 2022 Final Office Action dated Oct. 27, 2025.
U.S. Appl. No. 17/859,995, filed Jul. 7, 2022 Advisory Action dated Oct. 28, 2025.
U.S. Appl. No. 17/859,995, filed Jul. 7, 2022 Non-Final Office Action dated Dec. 23, 2025.
U.S. Appl. No. 17/881,270, filed Aug. 4, 2022 Final Office Action dated Oct. 27, 2025.
U.S. Appl. No. 18/273,163, filed Jul. 19, 2023 Restriction Requirement dated Nov. 6, 2025.
U.S. Appl. No. 18/289,341, filed Nov. 2, 2023 Restriction Requirement dated Nov. 6, 2025.
U.S. Appl. No. 19/068,969, filed Mar. 3, 2025 Non-Final Office Action dated Dec. 29, 2025.
U.S. Appl. No. 17/547,128, filed Dec. 9, 2021 Final Office Action dated Apr. 6, 2026.
U.S. Appl. No. 17/686,301, filed Mar. 3, 2022 Non-Final Office Action dated Apr. 3, 2026.
U.S. Appl. No. 17/691,990, filed Mar. 10, 2022 Final Office Action dated Mar. 9, 2026.
U.S. Appl. No. 17/694,416, filed Mar. 14, 2022 Final Office Action dated Apr. 9, 2026.
U.S. Appl. No. 17/697,879, filed Mar. 17, 2022 Non-Final Office Action dated Mar. 26, 2026.
U.S. Appl. No. 17/837,956, filed Jun. 10, 2022 Final Office Action dated Feb. 24, 2026.
U.S. Appl. No. 17/849,419, filed Jun. 24, 2022 Notice of Allowance dated Jan. 29, 2026.
U.S. Appl. No. 18/085,566, filed Dec. 20, 2022 Final Office Action dated Mar. 9, 2026.
U.S. Appl. No. 18/272,026, filed Jul. 12, 2023 Notice of Allowance dated Mar. 27, 2026.
U.S. Appl. No. 18/272,332, filed Jul. 13, 2023 Non-Final Office Action dated Mar. 25, 2026.
U.S. Appl. No. 18/272,332, filed Jul. 13, 2023 Restriction Requirement dated Jan. 21, 2026.
U.S. Appl. No. 18/273,163 filed Jul. 19, 2023 Non-Final Office Action dated Feb. 3, 2026.
U.S. Appl. No. 18/274,156, filed Jul. 25, 2023 Final Office Action dated Mar. 25, 2026.
U.S. Appl. No. 18/274,436, filed Jul. 26, 2023 Final Office Action dated Mar. 25, 2026.
U.S. Appl. No. 18/289,341, filed Nov. 2, 2023 Non-Final Office Action dated Feb. 18, 2026.
U.S. Appl. No. 18/715,504, filed May 31, 2024 Non-Final Office Action dated Apr. 9, 2026.
U.S. Appl. No. 18/715,504, filed May 31, 2024 Restriction Requirement dated Feb. 4, 2026.
U.S. Appl. No. 29/939,277, filed Apr. 25, 2024 Ex Parte Quayle Action dated Feb. 23, 2026.
U.S. Appl. No. 17/552,309, filed Dec. 15, 2021 Final Office Action dated Apr. 22, 2026.
U.S. Appl. No. 17/584,101, filed Jan. 25, 2022 Non-Final Office Action dated May 14, 2026.

(56) References Cited

OTHER PUBLICATIONS

U.S. Appl. No. 17/689,791, filed Mar. 8, 2022 Final Office Action dated Apr. 22, 2026.
U.S. Appl. No. 17/690,908, filed Mar. 9, 2022 Final Office Action dated May 12, 2026.
U.S. Appl. No. 17/691,990, filed Mar. 10, 2022 Advisory Action dated May 27, 2026.
U.S. Appl. No. 17/709,019, filed Mar. 30, 2022 Final Office Action dated Apr. 22, 2026.
U.S. Appl. No. 17/723,210, filed Apr. 18, 2022 Final Office Action dated May 5, 2026.
U.S. Appl. No. 17/837,956, filed Jun. 10, 2022 Notice of Allowance dated May 7, 2026.
U.S. Appl. No. 17/859,995, filed Jul. 7, 2022 Final Office Action dated Apr. 28, 202.
U.S. Appl. No. 18/085,566, filed Dec. 20, 2022 Advisory Action dated May 14, 2026.
U.S. Appl. No. 18/274,156, filed Jul. 25, 2023 Notice of Allowance dated Jun. 9, 2026.
U.S. Appl. No. 18/274,436, filed Jul. 26, 2023 Notice of Allowance dated Jun. 10, 2026.
U.S. Appl. No. 18/832,782, filed Jul. 24, 2024 Non-Final Office Action dated Apr. 20, 2026.
U.S. Appl. No. 18/837,098, filed Aug. 8, 2024 Non-Final Office Action dated Apr. 22, 2026.
U.S. Appl. No. 19/068,969, filed Mar. 3, 2025 Non-Final Office Action dated Apr. 28, 2026.
U.S. Appl. No. 29/939,277, filed Apr. 25, 2024 Notice of Allowance dated Jun. 10, 2026.

* cited by examiner 110
111
100
210
112
228
224
112
241
240
CHILLER TANK
214
CIRCULATION TANK
SUPPLY TANK
230
T
HEATER
T
T
215
225
227
235
236
T
FLOW SENSOR
238
P
237
211
221
CHILLER
PUMP
MIXING
PUMP
231
CIRCULATION
PUMP
FLUID
DELIVERY
LINE
212
CHILLER
CIRCUIT
232
CIRCULATING CIRCUIT
MIXING
CIRCUIT
130
222
CHILLER
213
120

6B
121
600
602
607
609
602
610
606
608
610
604
6B
121A
121B 121
612
616
624
618
620
600
622
150
614
607
626
628
629
627
603
121A
112
610
112
606
51

SYSTEMS, APPARATUS AND METHODS FOR LEAK PREVENTION WITH TARGETED TEMPERATURE MANAGEMENT GEL PADS

PRIORITY

This application claims the benefit of priority to U.S. Provisional Application No. 63/220,864, filed Jul. 12, 2021, which is incorporated by reference in its entirety into this application.

BACKGROUND

The effect of temperature on the human body has been well documented and the use of targeted temperature management (TTM) systems for selectively cooling and/or heating bodily tissue is known. Elevated temperatures, or hyperthermia, may be harmful to the brain under normal conditions, and even more importantly, during periods of physical stress, such as illness or surgery. Conversely, lower body temperatures, or mild hypothermia, may offer some degree of neuroprotection. Moderate to severe hypothermia tends to be more detrimental to the body, particularly the cardiovascular system.

Targeted temperature management can be viewed in two different aspects. The first aspect of temperature management includes treating abnormal body temperatures, i.e., cooling the body under conditions of hyperthermia or warming the body under conditions of hypothermia. The second aspect of thermoregulation is an evolving treatment that employs techniques that physically control a patient's temperature to provide a physiological benefit, such as cooling a stroke patient to gain some degree of neuroprotection. By way of example, TTM systems may be utilized in early stroke therapy to reduce neurological damage incurred by stroke and head trauma patients. Additional applications include selective patient heating/cooling during surgical procedures such as cardiopulmonary bypass operations.

TTM systems circulate a fluid (e.g., water) through one or more thermal contact pads coupled with a patient to affect surface-to-surface thermal energy exchange with the patient. In general, TTM systems comprise a TTM fluid control module coupled with at least one thermal contact pad via a fluid delivery line. In some embodiments, tubing extends from a thermal contact pad to couple with the fluid delivery line. One such TTM system is disclosed in U.S. Pat. No. 6,645,232, titled "Patient Temperature Control System with Fluid Pressure Maintenance" filed Oct. 11, 2001, and one such thermal contact pad and related system is disclosed in U.S. Pat. No. 6,197,045 titled "Cooling/heating Pad and System" filed Jan. 4, 1999, both of which are incorporated herein by reference in their entireties. As noted in the '045 patent, the ability to establish and maintain thermally intimate pad-to-patient contact is of importance to fully realizing medical efficacies with TTM systems.

A fluid delivery line generally includes at least two fluid conduits for transporting TTM fluid to and from the thermal contact pad. Fluid delivery lines may include connection systems for selectively connecting to and disconnecting from the thermal contact pad. Although TTM systems may include a functionality to purge a thermal contact pad prior to disconnecting the thermal contact pad from a fluid delivery line, an operator may fail to utilize such functionality and, even when utilized, such functionality may leave some TTM fluid in the thermal contact pad. As a result, upon disconnection, some TTM fluid may leak from the tubing extending from the thermal connection pad thereby causing health and safety risks. Disclosed herein are systems, devices, and methods for preventing leakage of TTM fluid upon disconnecting a thermal contact pad from a fluid delivery line.

SUMMARY OF THE INVENTION

Briefly summarized, disclosed herein is a targeted temperature management (TTM) system, comprising a TTM module configured to provide a TTM fluid, a fluid delivery line (FDL) including a FDL hub, a fluid delivery lumen and a fluid return lumen, and a pad configured to facilitate thermal energy transfer between the TTM fluid and a patient. The pad comprises a pad portion configured for placement on the patient, a fluid delivery conduit extending away from the pad portion, the fluid delivery conduit including (i) a delivery conduit connector at a proximal end thereof, and (ii) a first leak prevention valve configured to enable the TTM fluid to flow in a distal direction while preventing flow in a proximal direction, and a fluid return conduit extending away from the pad portion, the fluid return conduit including (i) a return conduit connector at a proximal end thereof, and (ii) a second leak prevention valve configured to enable the TTM fluid to flow in the proximal direction while preventing flow in the distal direction.

The pad further comprises a connector coupled to a distal end of each of the fluid delivery conduit and the fluid return conduit. The first and second leak prevention valves are located at a proximal end of the FDL. The first and second leak prevention are located at a distal end of the FDL. The first and second leak prevention valves are located at a distance from an end of the FDL within a range of 1-2 inches. The fluid delivery lumen includes the first leak prevention valve and a third leak prevention valve each configured to enable the TTM fluid to flow in the distal direction while preventing flow in the proximal direction, and the fluid return lumen includes the second leak prevention valve and a fourth leak prevention valve each configured to enable the TTM fluid to flow in the proximal direction while preventing flow in the distal direction. The first and second leak prevention valves are located at a proximal end of the FDL, and wherein the third and fourth leak prevention valves are located at a distal end of the FDL. The first through fourth leak prevention valves are located at a distance from a respective end of the FDL within a range of 1-2 inches. The first and second leak prevention valves are check valves and, in some embodiments, are duckbill valves.

Also discussed herein is a targeted temperature management (TTM) system comprising a TTM module configured to provide a TTM fluid, a fluid delivery line (FDL) including a FDL hub, a fluid delivery lumen and a fluid return lumen, wherein the fluid delivery lumen includes a first leak prevention valve configured to enable the TTM fluid to flow in a distal direction while preventing flow in a proximal direction, and wherein the fluid return lumen includes a second leak prevention valve configured to enable the TTM fluid to flow in the proximal direction while preventing flow in the distal direction, and a pad configured to facilitate thermal energy transfer between the TTM fluid and a patient.

Also discussed herein is a targeted temperature management (TTM) system comprising a TTM module configured to provide a TTM fluid, a fluid delivery line (FDL) including a FDL hub, a fluid delivery lumen and a fluid return lumen, and a pad configured to facilitate thermal energy transfer between the TTM fluid and a patient, the pad comprising a pad portion configured for placement on the patient including a first connection point including a first leak prevention valve and a second connection point including a second leak prevention valve, a fluid delivery conduit extending away from the pad portion, the fluid delivery conduit including a delivery conduit connector at a proximal end thereof and configured to couple with the first connection point, and a fluid return conduit extending away from the pad portion, the fluid return conduit including a return conduit connector at a proximal end thereof and configured to couple with the second connection point.

Also discussed herein is a targeted temperature management (TTM) system comprising a targeted temperature management (TTM) pad configured to facilitate thermal energy transfer between TTM fluid and a patient, the pad comprising a pad portion configured for placement on the patient including a first connection point including a first leak prevention valve and a second connection point including a second leak prevention valve, a fluid delivery conduit extending away from the pad portion, the fluid delivery conduit including a delivery conduit connector at a proximal end thereof and configured to couple with the first connection point, and a fluid return conduit extending away from the pad portion, the fluid return conduit including a return conduit connector at a proximal end thereof and configured to couple with the second connection point.

These and other features of the concepts provided herein will become more apparent to those of skill in the art in view of the accompanying drawings and the following description, which describe particular embodiments of such concepts in greater detail.

BRIEF DESCRIPTION OF DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION

Figure 1:
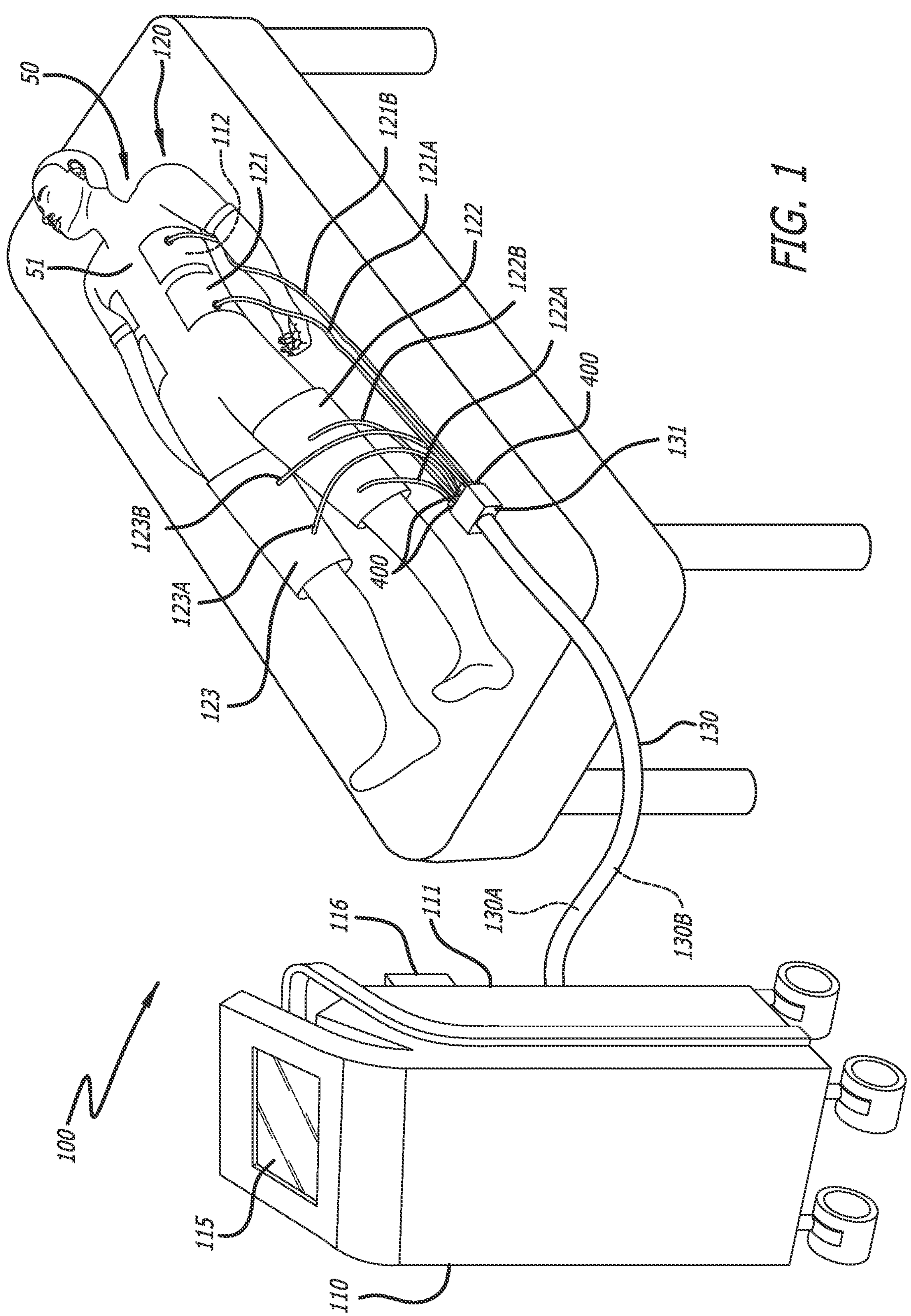
FIG. 1 illustrates a targeted temperature management (TTM) system for cooling or warming a patient, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," "horizontal," "vertical" and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise. The words "including," "has," and "having," as used herein, including the claims, shall have the same meaning as the word "comprising." Furthermore, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, components, functions, steps or acts are in some way inherently mutually exclusive.

The phrases "connected to" and "coupled with" refer to any form of interaction between two or more entities, including mechanical, electrical, magnetic, electromagnetic, fluid, signal, communicative (including wireless), and thermal interaction. Two components may be connected to or coupled with each other even though they are not in direct contact with each other. For example, two components may be coupled with each other through an intermediate component.

The directional terms "proximal" and "distal" are used herein to refer to opposite locations on a medical device. The proximal end of the device is defined as the end of the device closest to the end-user when the device is in use by the end-user. The distal end is the end opposite the proximal end, along the longitudinal direction of the device, or the end furthest from the end-user.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method. Additionally, all embodiments disclosed herein are combinable and/or interchangeable unless stated otherwise or such combination or interchange would be contrary to the stated operability of either embodiment.

Unless defined otherwise, all technical and scientific terms used herein have the same meaning as commonly understood by those of ordinary skill in the art.

FIG. 1 illustrates a targeted temperature management (TTM) system 100 connected to a patient 50 for administering TTM therapy to the patient 50, where the therapy may include a cooling and/or warming of the patient 50, in accordance with some embodiments. The TTM system 100 includes a TTM module 110, a fluid delivery line (FDL) 130, and a thermal contact pad set 120. In the illustrated embodiment, the pad set 120 includes three thermal contact pads (pads) 121, 122, 123. In other embodiments, the pad set 120 may include one or more thermal contact pads (e.g., any number). In the illustrated embodiments, the FDL 130 is configured to couple with two thermal pads. In other embodiments, the FDL 130 may be configured to couple with one or more thermal contact pads. In some embodiments, the system 100 may include more than one FDL 130.

Each pad includes a fluid delivery conduit and a fluid return conduit (sometimes referred to generally as the fluid conduits) coupled with the FDL 130 via an FDL hub 131. The FDL 130 includes a fluid delivery lumen 130A and a fluid return lumen 130B. In the illustrated embodiment, the pad 121 includes the fluid delivery conduit 121A coupled with the FDL 130 so as to be in fluid communication with the fluid delivery lumen 130A and a fluid return conduit 121B coupled with the FDL 130 so as to be in fluid communication with the fluid return lumen 130B. Similarly, the pad 122 includes the fluid delivery conduit 122A coupled with the FDL 130 so as to be in fluid communication with the fluid delivery lumen 130A and a fluid return conduit 122B coupled with the FDL 130 so as to be in fluid communication with the fluid return lumen 130B. Further, the pad 123 includes the fluid delivery conduit 123A coupled with the FDL 130 so as to be in fluid communication with the fluid delivery lumen 130A and a fluid return conduit 123B coupled with the FDL 130 so as to be in fluid communication with the fluid return lumen 130B. The proximal ends of the conduits 121A, 121B, the conduits 122A, 122B, and the conduits 123A, 123B may each terminate at a pad connector 400 discussed in detail below.

In use, the TTM module 110 prepares the TTM fluid 112 for delivery to the pad set 120 by heating or cooling the TTM fluid 112 to a defined temperature in accordance with prescribed TTM therapy parameters input by clinician via a graphical user interface 115. The TTM module 110 circulates the TTM fluid 112 between the TTM module 110 and the pad set 120 via the FDL 130. The pad set 120 is applied to the skin 51 of the patient to facilitate thermal energy exchange between the pad set 120 and the patient 50. During the TTM therapy, the TTM module 110 may continually control the temperature of the TTM fluid 112 toward a target temperature. The TTM module 110 may further include a pad identification interface 116 as further described below in relation to FIG. 3

Figure 2:
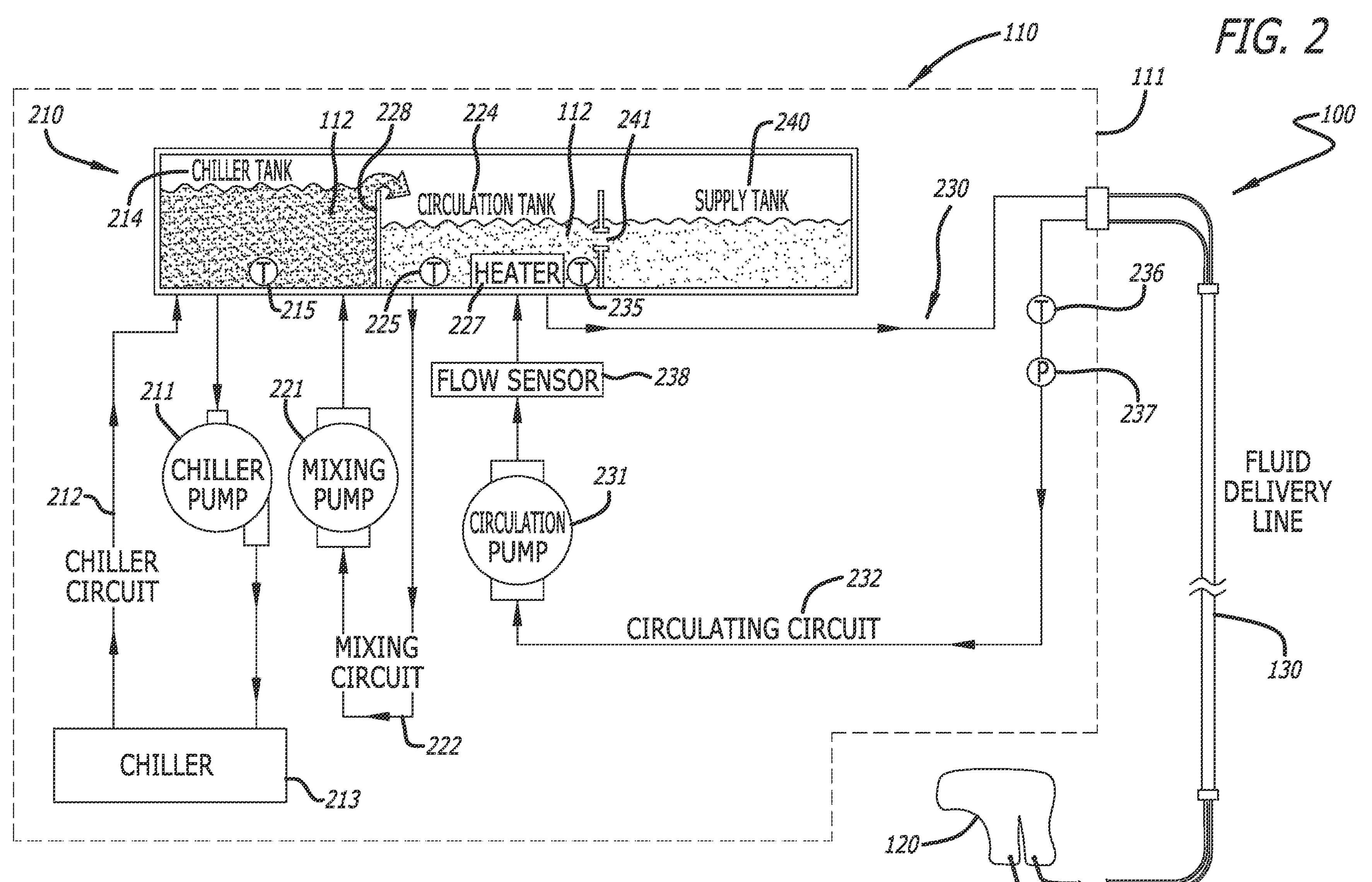
FIG. 2 illustrates a hydraulic schematic of the TTM system of FIG. 1, in accordance with some embodiments.

FIG. 2 illustrates a hydraulic schematic of the TTM system 100. The pad set 120 (FIG. 1) along with the corresponding fluid conduits are disposed external to the housing 111 of the TTM module 110. The TTM module includes various fluid sensors and fluid control devices to prepare and circulate the TTM fluid 112. The fluid subsystems of the TTM module may include a temperature control subsystem 210 and a circulation subsystem 230.

The temperature control subsystem 210 may include a chiller pump 211 to pump (recirculate) TTM fluid 112 through a chiller circuit 212 that includes a chiller 213 and a chiller tank 214. A temperature sensor 215 within the chiller tank 214 is configured to measure a temperature of the TTM fluid 112 within the chiller tank 214. The chiller 213 may be controlled by a temperature control logic (see FIG. 3) as further described below to establish a desired temperature of the TTM fluid 112 within chiller tank 214. In some instances, the temperature of the TTM fluid 112 within the chiller tank 214 may be less than the target temperature for the TTM therapy.

The temperature control subsystem 210 may further include a mixing pump 221 to pump TTM fluid 112 through a mixing circuit 222 that includes the chiller tank 214, a circulation tank 224, and a dam 228 disposed between the chiller tank 214 and circulation tank 224. The TTM fluid 112, when pumped by the mixing pump 221, enters the chiller tank 214 and mixes with the TTM fluid 112 within the chiller tank 214. The mixed TTM fluid 112 within the chiller tank 214 flows over the dam 228 and into the circulation tank 224. In other words, the mixing circuit 222 mixes the TTM fluid 112 within chiller tank 214 with the TTM fluid 112 within circulation tank 224 to cool the TTM fluid 112 within the circulation tank 224. A temperature sensor 225 within the circulation tank 224 measures the temperature of the TTM fluid 112 within the circulation tank 224. The temperature control logic may control the mixing pump 221 in accordance with temperature data from the temperature sensor 225 within the circulation tank 224.

The circulation tank 224 includes a heater 227 to increase to the temperature of the TTM fluid 112 within the circulation tank 224, and the heater 227 may be controlled by the temperature control logic. In summary, the temperature control logic when executed by the processor (see FIG. 3) may 1) receive temperature data from the temperature sensor 215 within the chiller tank and the temperature sensor 225 within the circulation tank 224, and 2) control the operation of the chiller 213, the chiller pump 211, the heater 227, and mixing pump 222 to establish and maintain the temperature of the TTM fluid 112 within the circulation tank 224 at the target temperature for the TTM therapy.

The circulation subsystem 230 includes a circulation pump 213 to pull TTM fluid 112 from the circulation tank 224 and through a circulating circuit 232 that includes the pad set 120 located upstream of the circulation pump 213. The circulating circuit 232 also includes a pressure sensor 237 to represent a pressure of the TTM fluid 112 within the pad set 120. The circulating circuit 232 includes a temperature sensor 235 within the circulation tank 224 to represent the temperature of the TTM fluid 112 entering the pad set 120 and a temperature sensor 236 to represent the temperature of the TTM fluid exiting the pad set 120. A flow meter 238 is disposed downstream of the circulation pump 213 to measure the flow rate of TTM fluid 112 through the circulating circuit 232 before the TTM fluid 112 re-enters that the circulation tank 224.

In use, the circulation tank 224, which may be vented to atmosphere, is located below (i.e., at a lower elevation than) the pad set 120 so that a pressure within the pad set 120 is less than atmospheric pressure (i.e., negative) when TTM fluid flow through the circulating circuit 232 is stopped. The pad set 120 is also placed upstream of the circulation pump 231 to further establish a negative pressure within the pad set 120 when the circulation pump 213 is operating. The fluid flow control logic (see FIG. 3) may control the operation of the circulation pump 213 to establish and maintain a desired negative pressure within the pad set 120. A supply tank 240 provides TTM fluid 112 to the circulation tank 224 via a port 241 to maintain a defined volume of TTM fluid 112 within the circulation tank 224.

Figure 3:
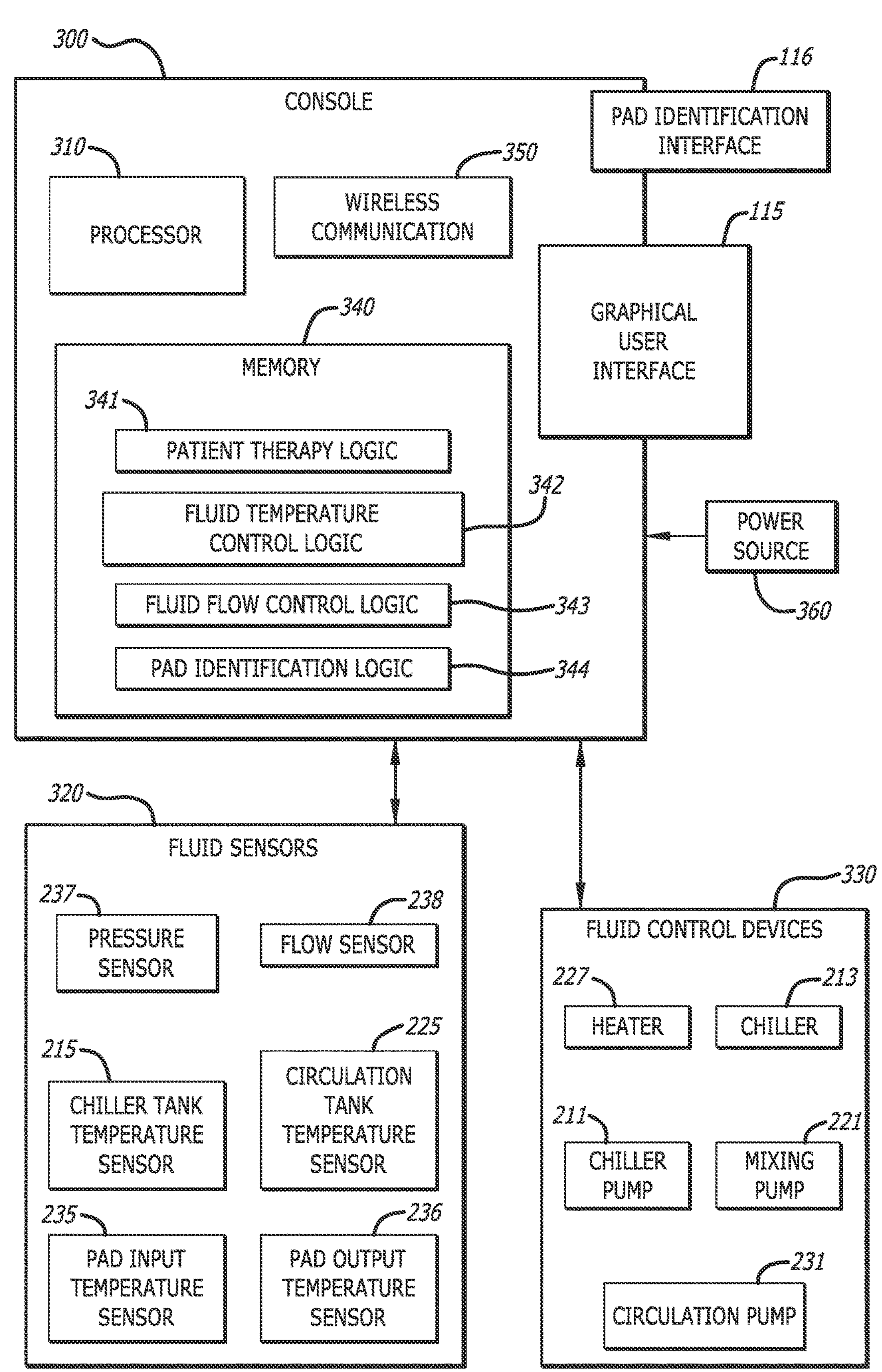
FIG. 3 illustrates a block diagram depicting various elements of a console of the TTM module of FIG. 1, in accordance with some embodiments.

FIG. 3 illustrates a block diagram depicting various elements of the TTM module 110 of FIG. 1, in accordance with some embodiments. The TTM module 110 includes a console 300 including a processor 310 and memory 340 including non-transitory, computer-readable medium. Logic modules stored in the memory 340 include patient therapy logic 341, fluid temperature control logic 342, fluid flow control logic 343, and pad identification logic 344. The logic modules when executed by the processor 310 define the operations and functionality of the TTM Module 110.

Illustrated in the block diagram of FIG. 3 are fluid sensors 320 as described above in relation to FIG. 2. Each of the fluid sensors 320 are coupled with the console 300 so that data from the fluid sensors 320 may be utilized in the performance of TTM module operations. Fluid control devices 330 are also illustrated in FIG. 3 as coupled with the console 300. As such, logic modules may control the operation of the fluid control devices 330 as further described below.

The patient therapy logic 341 may receive input from the clinician via the GUI 115 to establish operating parameters in accordance with a prescribed TTM therapy. Operating parameters may include a target temperature for the TTM fluid 112 and/or a thermal energy exchange rate which may include a time-based target temperature profile. In some embodiments, the fluid temperature control logic 342 may define other fluid temperatures of the TTM fluid 112 within the TTM module 110, such a target temperature for the TTM fluid 112 within the chiller tank 214, for example.

The fluid temperature control logic 342 may perform operations to establish and maintain a temperature of the TTM fluid 112 delivered to the pad set 120 in accordance with the predefined target temperature. One temperature control operation may include chilling the TTM fluid 112 within the chiller tank 214. The fluid temperature control logic 342 may utilize temperature data from the chiller tank temperature sensor 215 to control the operation of the chiller 213 to establish and maintain a temperature of the TTM fluid 112 within the chiller tank 214.

Another temperature control operation may include cooling the TTM fluid 112 within the circulation tank 224. The fluid temperature control logic 342 may utilize temperature data from the circulation tank temperature sensor 225 to control the operation of the mixing pump 221 to decrease the temperature of the TTM fluid 112 within the circulation tank 224 by mixing TTM fluid 112 from the chiller tank 214 with TTM fluid 112 within circulation tank 224.

Still another temperature control operation may include warming the TTM fluid 112 within the circulation tank 224. The fluid temperature control logic 342 may utilize temperature data from the circulation tank temperature sensor 225 to control the operation of the heater 227 to increase the temperature of the TTM fluid 112 within the circulation tank 224.

The fluid flow control logic 343 may control the operation of the circulation pump 231. As a thermal energy exchange rate is at least partially defined by the flow rate of the TTM fluid 112 through the pad set 120, the fluid flow control logic 343 may, in some embodiments, control the operation of the circulation pump 231 in accordance with a defined thermal energy exchange rate for the TTM therapy.

The console 300 may include or be coupled with a wireless communication module 350 to facilitate wireless communication with external devices. A power source 360 provides electrical power to the console 300.

The identification interface 116 may be coupled with the console 300 and provide pad identification data to the pad identification logic 344. The pad identification logic 344 may be configured so that, when executed by the processor 310, pad identification logic 344 may alert the clinician as to the identification of each thermal pad of the pad set 120. In an embodiment, the pad identification logic 344 may alert the clinician that one or more pads were not manufactured by a defined set of manufacturers. For example, if the identification interface 116 does not receive any pad identification data, the pad identification logic 344 may alert the clinician accordingly.

In some embodiments, the identification data may include a set of identification parameters (e.g., pad size), and the memory may include a corresponding set of identification parameters. An operation of the pad identification logic 344 may include comparing an identification parameter of the identification data with a corresponding identification parameter stored in memory, and the identification logic may be configured to modify the operation of the system in accordance with a result of the comparison.

Figure 4:
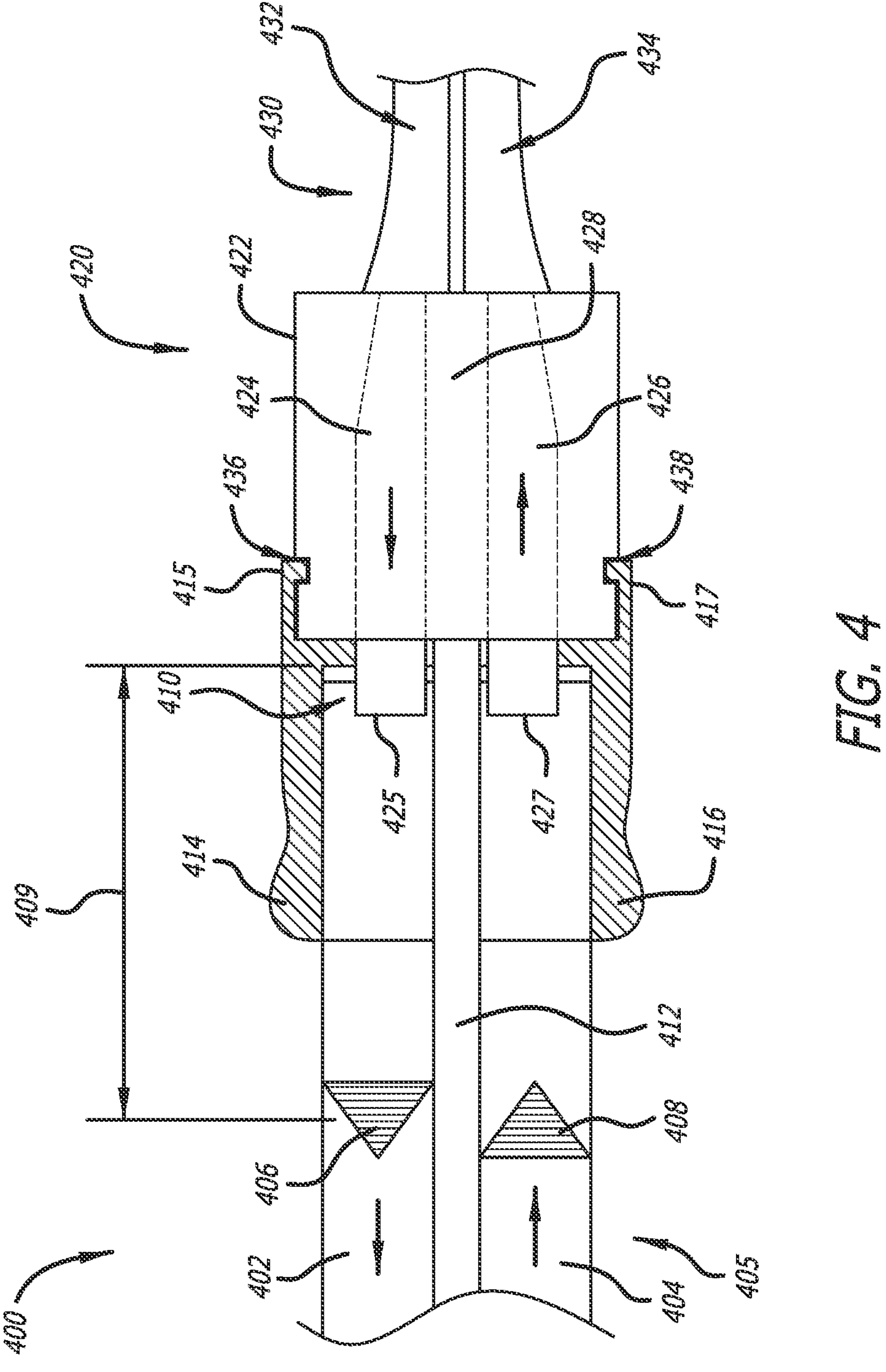
FIG. 4 is a view of a proximal portion of a pad connector and a fluid delivery line hub shown in a connected state, in accordance with some embodiments.

FIG. 4 is a cross-sectional view of a proximal portion of the pad connector 400 and a fluid delivery line hub 420 shown in a connected state, in accordance with some embodiments. The FDL hub 420 may be one specific embodiment of the FDL hub 131 of FIG. 1, and the pad connector 400 may be disposed at the proximal end of a pair of fluid delivery and fluid return conduits, such as the conduits 121A, 121B (illustrated as conduits 402, 404 in FIG. 4).

As the pad connector 400 connects with the FDL hub 420, the distal conduit tips 425, 427 enter the conduits 402, 404, respectively, as discussed below. The pad connector 400 includes a first (delivery) conduit 402 having a first leak prevention valve 406, a second (return) conduit 404 having a second leak prevent valve 408, a first (top side) compression strip 414 having a latch 415 and a second (bottom side) compression side 416 having a latch 417. The valves 406, 408 may be located near the proximal end of the conduits 402, 404. In some embodiments, the valves 406, 408 are each located a distance 409 from the distal end of the conduits 402, 404, where the distance 409 may be, for example, 0.5 inches, 1 inch, 1.5 inches, 2 inches, etc. However, it is noted that the valves 406, 408 need not be located at the same distance from the distal tip of the respective conduit as each other.

The two conduits 402, 404 are shown where one of the conduits may be configured to receive TTM fluid from a fluid delivery conduit (e.g., of the FDL hub 420) and the other conduit may be configured to return TTM fluid to a fluid return conduit (e.g., of the FDL hub 420). However, in some embodiments, the pad connector 400 may include a single conduit such that multiple pad connectors are utilized where a first such pad connector is configured to delivery TTM fluid and a second such pad connector is configured to return TTM fluid.

As noted above, in current technology, when a pad connector is disconnected from a FDL hub (or an alternative TTM fluid source), there is often a problem with excess TTM fluid that leaks from the pad connector. Specifically, TTM fluid that remains in the tubing connected to the pad connector often drips out of the proximal end (e.g., opposite the pad), which may lead to health and safety concerns. However, inclusion of the leak prevention valves 406, 408 within the conduits 402, 404 prevent the excess TTM fluid from exiting the conduits 402, 404 when the pad connector 400 is disconnected from the FDL hub 420. Examples of the leak prevention valves 406, 408 (and other valves discussed herein) include various check valves such as duckbill valves, swing check valves, tilting disc check valves, etc.

As the TTM fluid flows from the delivery conduit 424 of the FDL hub 420 into the delivery conduit 402, the TTM fluid passes through the valve 406. Similarly, as the TTM fluid flows from the return conduit 404 into the return conduit 426 of the FDL hub 420, the TTM fluid passes through the valve 408. Further, as the TTM system (e.g., the TTM system 100) operates under a pressure (e.g., negative pressure), the TTM fluid flows at a rate configured to pass through the valves 406, 408. However, based on the operation of the valves 406, 408, the TTM fluid cannot flow in reverse (e.g., from the delivery conduit 402 to the FDL hub 420 and/or from the FDL hub 420 to the return conduit 404), where the operation of check valves is well-known. Additionally, some flow rate or pressure is required for the TTM fluid to pass through the valves 406, 408; thus, when the pad connector 400 is disconnected from the FDL hub 420 and pressure is not present, any TTM fluid within the pad 121 and/or tubing 405 will be unable to pass through either valve 406, 408.

Still referring to FIG. 4, the latches 415, 417 extend proximally from a proximal end of the pad connector 400 (e.g., toward a TTM module such as the module 110 of FIG. 1). As is shown, the latches 415, 417 align with the grooves 436, 438 such that upon application of pressure to the compression strips 414, 416 of the pad connector 400, the latches 415, 417 move in opposing directions allowing the pad connector 400 to physically connect with the FDL hub 420. Stated differently, the compression strips 414, 416 are configured to receive an application of pressure, which causes movement of the latches 415, 417 in opposing directions (e.g., away from the FDL hub 420) thereby allowing the pad connector 400 to connect with and disconnect from the FDL hub 420.

As is understood, upon removal of the pressure from the compression strips 414, 416, the latches 415, 417 will return to a default position, which is within the grooves 436, 438 when the pad connector 400 is connected with the FDL hub 420. Further, the conduit 424 aligns with the conduit 402 and the conduit 426 aligns with the conduit 404 thereby providing for fluid communication between the pad connector 400 and the FDL hub 420. In some embodiments, the proximal ends of the conduits 402, 404 may include an elastomeric ring 410 surrounding the conduit openings such that a fluid seal is established between the rings 410 and the distal conduit tips 425, 427 when inserted into the conduits 402, 404.

Additionally, tubing 405 extends from a distal end of from the pad connector 400 (e.g., toward a TTM pad such as the pad 121). It is further illustrated that a conduit partition 412 is disposed within the connector 400 separating the conduits 402, 404.

The embodiment of the FDL hub 420 illustrated in FIG. 4 includes a set of fluid conduits including a first fluid conduit 424 that may deliver TTM fluid to the pad connector 400 and a second fluid conduit 426 that may receive return TTM fluid from the pad connector 400. It is noted that the set of fluid conduits 424, 426 may be one of a plurality of sets of fluid conduits. More specifically, the FDL hub 420 may be configured to couple with a plurality of pad connectors such that each pad connector couples to a set of fluid conduits similar to the set of fluid conduits 424, 426, wherein the plurality of sets of fluid conduits and corresponding pad connectors are illustrated in FIG. 1.

FIG. 4 provides a side cross-sectional view of the fluid delivery line hub 420, which illustrates that the FDL hub 420 includes a housing 422 that houses the set of fluid conduits 424, 426. The housing 422 includes two grooves 436, 438 on opposing sides (e.g., on a top side and a bottom side). As is shown, the latches 415, 417 are disposed within the grooves 436, 438 when the pad connector 400 is connected to the FDL hub 420.

Additionally, the cross-sectional view of FIG. 4 illustrates that the conduits 424, 426 extend distally from the housing 422 (e.g., toward a TTM pad), where the distally extending portions may be referred to as distal conduit tips (e.g., the distal conduit tips 425, 427). Further, the cross-sectional view of FIG. 4 illustrates tubing 430 that extends proximally from the housing 422 (e.g., toward a TTM module such as the module 110 of FIG. 1), where the tubing 430 may be comprised of a delivery tubing 432 and a return tubing 434. In some embodiments, when the FDL hub 420 includes a plurality of sets of conduits, each of the delivery fluid conduits may receive TTM fluid from the delivery tubing 432 and each of the plurality of return fluid conduits may return TTM fluid to the return tubing 434.

Figure 5:
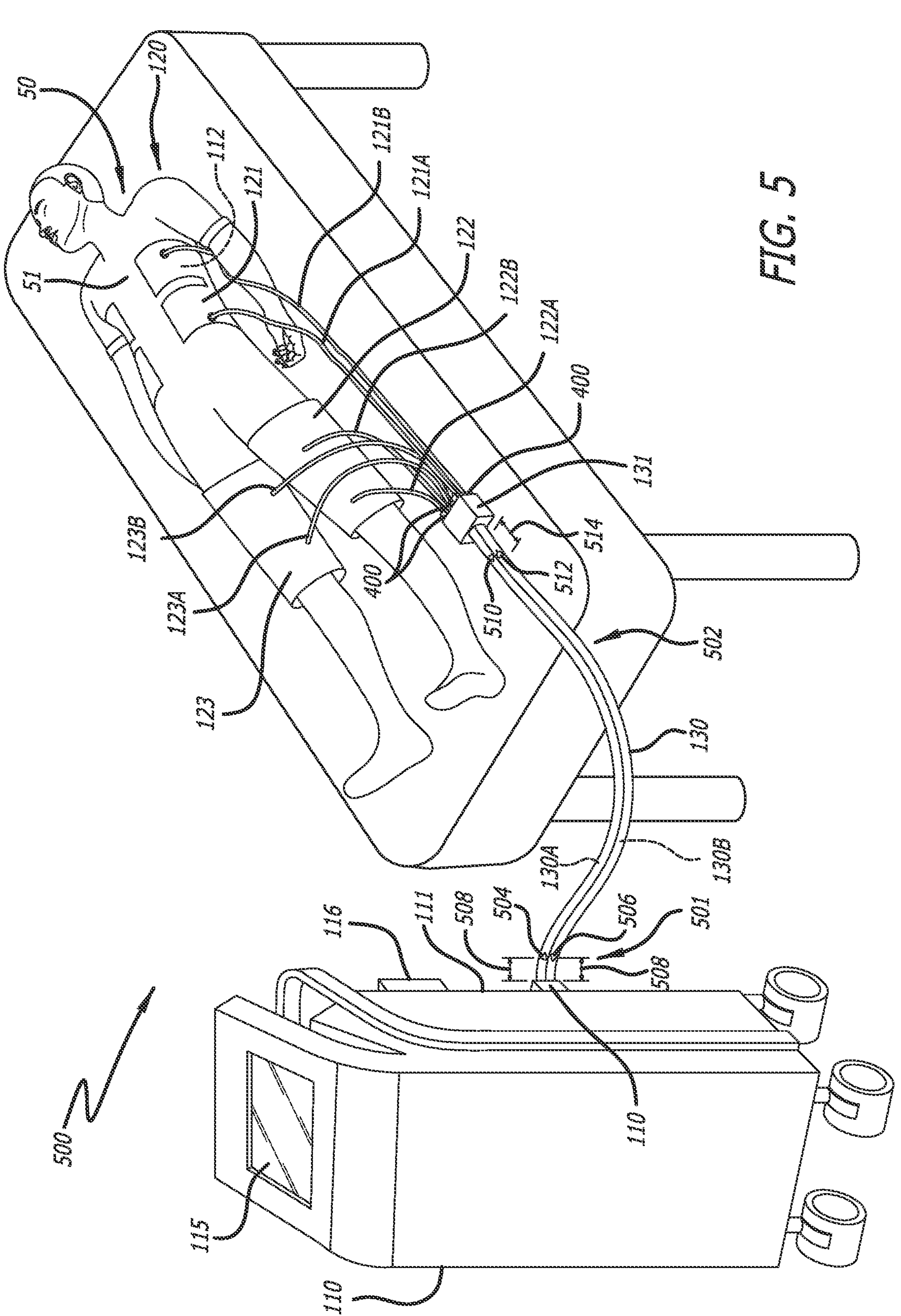
FIG. 5 illustrates an embodiment of a TTM system for cooling or warming a patient including a plurality of leak prevention valves, in accordance with some embodiments.

FIG. 5 illustrates an embodiment of a TTM system for cooling or warming a patient including a plurality of leak prevention valves, in accordance with some embodiments. The TTM system 500 of FIG. 5 provides one embodiment of the TTM system 100 in which leak prevention valves are included within the FDL 130. Specifically, FIG. 5 illustrates that the FDL 130 may include a set of leak prevention valves at either or both of a proximal end 501 or a distal end 502. Further, either TTM system 100, 500 may be utilized while also deploying the embodiments illustrated in FIGS. 4 and 6A-6B.

With respect to the proximal end 501, leak prevention valves 504, 506 may be included within the FDL 130, with a first leak prevention valve 504 inserted within the fluid delivery lumen 130A and a second leak prevention valve 506 inserted within the fluid return lumen 130B. Similar to the discussion above with respect to FIG. 4, the leak prevention valves 504, 506 prevent TTM fluid that remains within the lumens 130A, 130B from dripping out of the proximal end of the FDL 130 when disconnected from the TTM module 110.

Further, with respect to the distal end 502, leak prevention valves 510, 512 may be included within the FDL 130, with a third leak prevention valve 510 inserted within the fluid delivery lumen 130A and a fourth leak prevention valve 512 inserted within the fluid return lumen 130B. Similar to the discussion above with respect to FIG. 4, the leak prevention valves 510, 512 prevent TTM fluid that remains within the lumens 130A, 130B from dripping out of the distal end of the FDL 130 when disconnected from an FDL hub, such as from either of the FDL hub 131, 420 of FIGS. 1 and 4, respectively. Examples of the leak prevention valves 510, 512 include various check valves such as duckbill valves, swing check valves, tilting disc check valves, etc.

The valves 504, 506 may be located near the proximal end 501 of the FDL 130 while the valves 510, 512 are located near the distal end of the FDL 130. In some embodiments, the valves 504, 506 are each located a distance 508 from the proximal end 501 and the valves 510, 512 are each located a distance 514 from the proximal end 501, where the distances 508, 514 may be, for example, 0.5 inches, 1 inch, 1.5 inches, 2 inches, etc. However, it is noted that the valves 504, 506, 510, 512 need not be located at the same distance from the distal tip of the respective lumen as one another.

As the TTM fluid flows from the TTM module 110 into the fluid delivery lumen 130A, the TTM fluid passes through the valve 504, and as the TTM fluid flows from the fluid return lumen 130B into the TTM module 110, the TTM fluid passes through the valve 506. Additionally, during operation of the TTM system 500, the TTM fluid flows from fluid delivery lumen 130A to the FDL hub 131 while passing through the valve 510 and flows from the FDL hub 131 into the fluid return lumen 130B while passing through the valve 512. Further, as the TTM system (e.g., the TTM system 500) operates under a pressure (e.g., negative pressure), the TTM fluid flows at a rate configured to pass through the valves 504, 506, 510, 512.

However, based on the operation of the valves (e.g., operating in accordance with known check valve operability), the TTM fluid cannot flow in reverse (e.g., from the fluid delivery lumen 130A to the TTM module 110 and/or from the TTM module 110 to the fluid return lumen 404). Additionally, some flow rate or pressure is required for the TTM fluid to pass through the valves 504, 506, 510, 512. Therefore, when the FDL 130 is disconnected from the TTM module 110, the pressure under which the system was operating will no longer present and as a result, any TTM fluid within the FDL 130 will be unable to pass through either valve 504, 506. Additionally, when the FDL 130 is disconnected from the FDL hub 131, the pressure under which the system was operating will no longer present to pull TTM fluid from the pad 121 into the FDL 130, will be unable to pull TTM fluid from the TTM module 110 into the FDL 130 and any TTM fluid remaining in the fluid return lumen 130B will be pulled under negative pressure into the TTM module 110. As a result, TTM fluid will not be able to pass through any of the valves 504, 510 or 512, thereby preventing leakage of the TTM fluid.

Figure 6A:
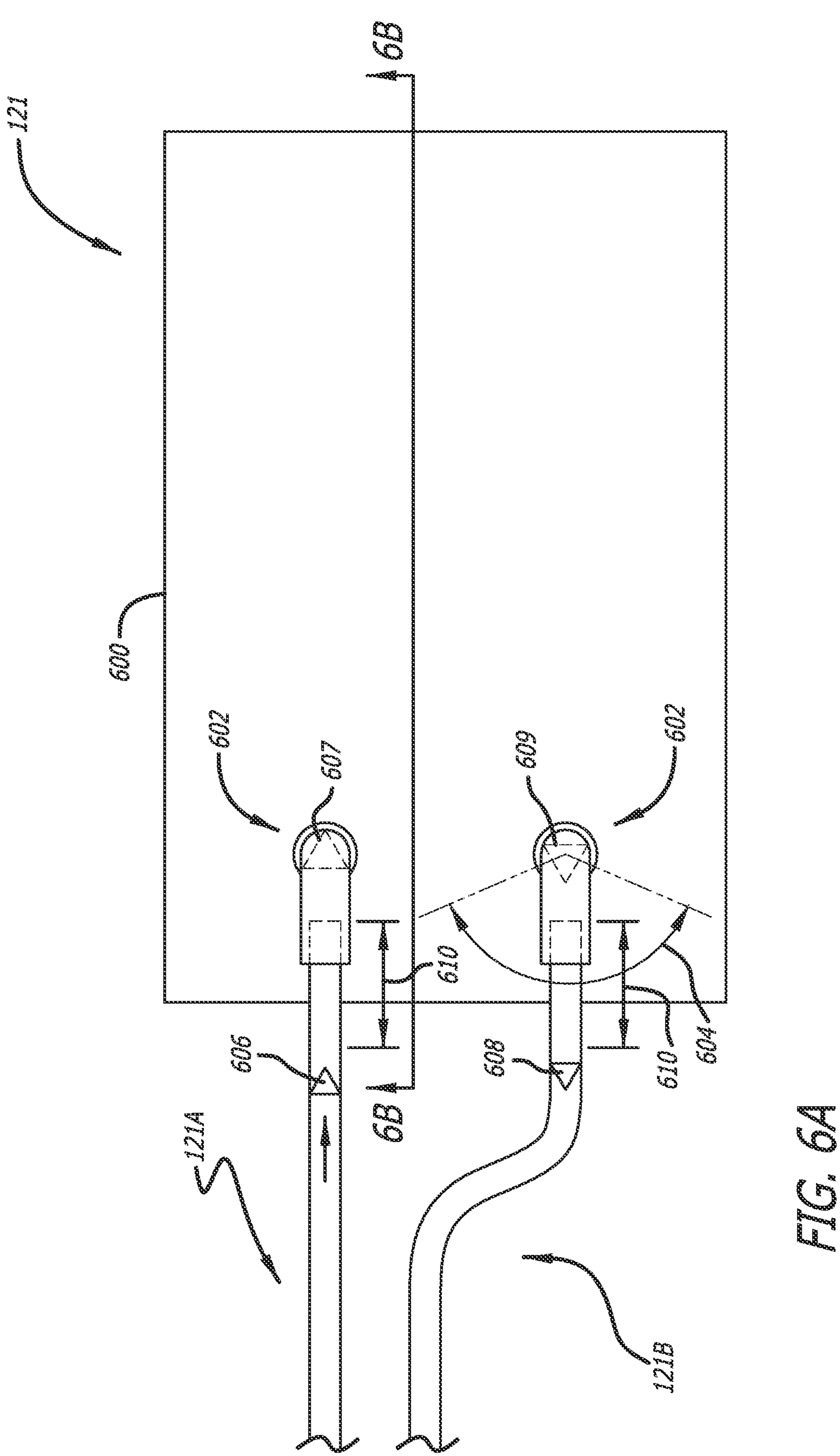
FIG. 6A is a top view of a thermal pad of the system of either FIG. 1 or 5, in accordance with some embodiments.

FIG. 6A is a top view of a thermal pad, in accordance with some embodiments. While the description that follows describes features, components and details of the pad 121, the description that follows may equally apply to any and all other thermal contact pads of the pad set 120. The fluid delivery conduit 121A and the fluid return conduit 121B extend away from the joints 602 and include leak prevention valves 606, 608, in accordance with some embodiments. The valves 606, 608 may be located near the distal end 628 of the conduits 121A, 121B, such as a distance 610 from the distal end 628 of, for example, 0.5 inches, 1 inch, 1.5 inches, 2 inches, etc.

As the TTM fluid flows from the fluid delivery conduit 121A into the pad 121, the TTM fluid passes through the valve 606, and as the TTM fluid flows from the pad 121 into the fluid return conduit 121B, the TTM fluid passes through the valve 608. Additionally, during operation, the TTM system, e.g., either the TTM system 100 or 500, operates under a pressure (e.g., negative pressure) such that the TTM fluid flows at a rate configured to pass through the valves 606, 608.

Based on the operation of the valves, the TTM fluid cannot flow in reverse. Additionally, some flow rate or pressure is required for the TTM fluid to pass through the valves 606, 608. Therefore, when the either of the conduits 121A, 121B is disconnected from the pad 121, the pressure under which the system was operating will no longer present and as a result, any TTM fluid within the pad 121 and/or the conduits 121A, 121B will be unable to pass through either valve 606, 608, thereby preventing leakage of the TTM fluid.

Still referring to FIG. 6A, the joints 602 may provide for a rotatable connection between fluid delivery conduit 121A and the fluid return conduit 121B and a pad portion 600 of the pad 121. The rotatable connection may provide for the fluid conduit to rotate through an angle 604 ranging up to about 90 degrees, 180 degrees, 360 degrees, etc. In some embodiments, the joint 602 may define a fixed rotatable connection, i.e., the joint may allow rotation but not separation. In other embodiments, the joint 602 may define a pre-assembled rotatable connection that allows rotation and separation by the clinician.

FIG. 6A also illustrates placement of two optional valves 607, 609, which may be utilized in combination with, or in place of, the valves 606, 608. The valves 607, 609 operate in the same manner as the valves 606, 608 but are located more distally than the valves 606, 608. The valves 607, 609 may be configured as components of the pad 121 as opposed to components included within the conduits 121A, 121B.

Figure 6B:
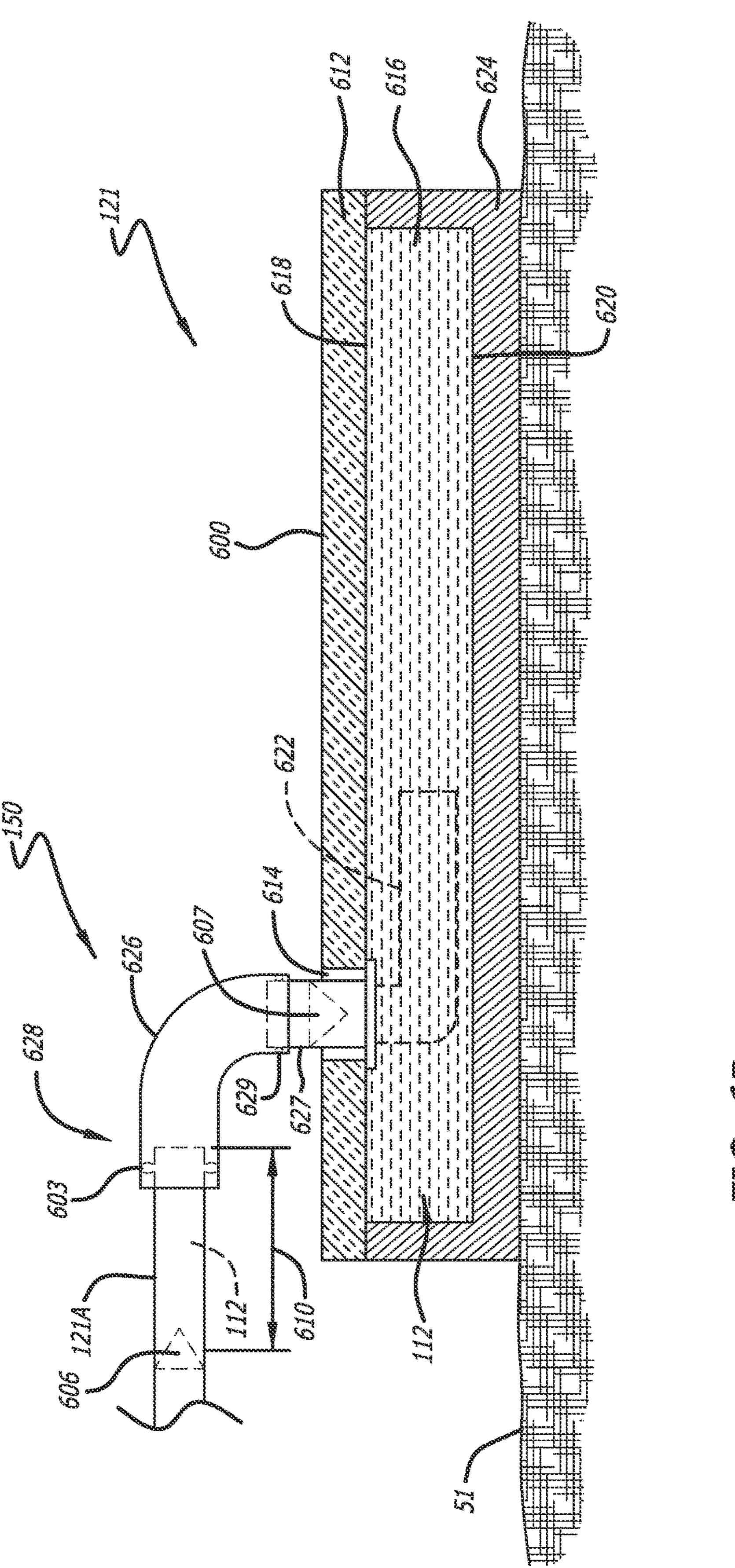
FIG. 6B is a cross-sectional view of the pad of FIG. 6A cut along sectioning lines 6B-6B, in accordance with some embodiments.

FIG. 6B provides a cross-sectional view of the pad of FIG. 6A cut along sectioning lines 6B-6B, in accordance with some embodiments. The pad 121 may include multiple layers including a fluid containing layer 616 that is fluidly coupled with the fluid delivery conduit 121A via the joint 602 to facilitate circulation of the TTM fluid 112 within the fluid containing layer 616. Similarly, (although not shown in FIG. 6B) the fluid containing layer 616 is fluidly coupled with the fluid return conduit 121B via a second joint 602 (see FIG. 6A). In some embodiments, the proximal ends of each joint 602 may include an elastomeric ring 603 surrounding the proximal openings such that a fluid seal is established between the rings 603 and the distal tips of the conduits 121A, 121B when inserted into the joints 602.

The fluid containing layer 616 having TTM fluid 112 circulating therein defines a heat sink or a heat source for the patient 50 in accordance with a temperature of the TTM fluid 112. The fluid delivery conduit 121A may also be coupled with an internal fluid conduit 622 of the fluid containing layer 616 so that TTM fluid 112 entering the fluid containing layer 616 passes through the internal fluid conduit 622.

The pad 121 may include a thermal conduction layer 624 disposed between the fluid containing layer 616 and the patient 50. The thermal conduction layer 624 is configured to facilitate thermal energy transfer between the fluid containing layer 616 and the patient 50. The thermal conduction layer 624 may be attached to the fluid containing layer 616 along a bottom surface 620 of the fluid containing layer 616. The thermal conduction layer 624 may be conformable to provide for intimate contact with the patient 50. In other words, the thermal conduction layer 624 may conform to a contour of the patient 50 to inhibit the presence of space or air pockets between the thermal conduction layer 624 and the patient 50.

The pad 121 may include an insulation layer 612 disposed on the top side of the fluid containing layer 616. The insulation layer 612 is configured to inhibit thermal energy transfer between the fluid containing layer 616 and the environment. The insulation layer 612 may be attached to the fluid containing layer 616 along a top surface 618 of the fluid containing layer 616. In some embodiments, the insulation layer 612 may include one or more openings 614 extending through the insulation layer 612 to provide for coupling of the fluid delivery conduit 121A and fluid return conduit 121B with the fluid containing layer 616.

As noted above with respect to the discussion of FIG. 6A, the embodiment illustrated in FIGS. 6A-6B may include valves 607, 609 with the valve 607 illustrated in FIG. 6B. As shown, a delivery conduit connection point 627 (connection point 627) is shown extending between the distal end of the joint 602 and the pad 121. The valve 607 may be located within the connection point 627 to prevent any TTM fluid from flowing out of the pad 121 when the fluid delivery conduit 121A is disconnected therefrom (and/or if the joint 626 is removable and disconnected therefrom). In some embodiments (when the joints 602 are removably couplable from with the pad 121), the distal ends of each joint 602 may include an elastomeric ring 629 surrounding the distal openings such that a fluid seal is established between the rings 629 and conduits extending from the pad 121, such as the connection point 627, when the joint 602 and the connection point 627 are coupled.

The joint 602 may include an elbow 626 to change the orientation of the fluid delivery conduit 121A. As shown, the orientation of the fluid delivery conduit 121A is shifted from an orientation that is parallel to the pad 121 to an orientation that is substantially perpendicular to the pad 121.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

What is claimed is:

1. A targeted temperature management (TTM) system, comprising:

a TTM module configured to provide a TTM fluid;

a fluid delivery line (FDL) including a FDL hub, a fluid delivery lumen and a fluid return lumen, wherein the fluid delivery lumen includes a first leak prevention valve and a third leak prevention valve each configured to enable the TTM fluid to flow in a distal direction while preventing flow in a proximal direction, and wherein the fluid return lumen includes a second leak prevention valve and a fourth leak prevention valve each configured to enable the TTM fluid to flow in the proximal direction while preventing flow in the distal direction; and a pad configured to facilitate thermal energy transfer between the TTM fluid and a patient.

2. The TTM system of claim 1, wherein the pad comprises:

a pad portion configured for placement on the patient, a fluid delivery conduit extending away from the pad portion, the fluid delivery conduit including a delivery conduit connector at a proximal end thereof, and a fluid return conduit extending away from the pad portion, the fluid return conduit including a return conduit connector at a proximal end thereof, and a connector coupled to a distal end of each of the fluid delivery conduit and the fluid return conduit.

3. The TTM system of claim 1, wherein the first leak prevention valve and the second leak prevention valve are located at a proximal end of the FDL.

4. The TTM system of claim 1, wherein the first leak prevention valve and the second leak prevention valve are located at a distal end of the FDL.

5. The TTM system of claim 1, wherein the first leak prevention valve and the second leak prevention valve are located at a distance from an end of the FDL within a range of 1-2 inches.

6. The TTM system of claim 1, wherein the first leak prevention valve and the second leak prevention valve are located at a proximal end of the FDL, and wherein the third leak prevention valve and the fourth leak prevention valve are located at a distal end of the FDL.

7. The TTM system of claim 1, wherein the first leak prevention valve through the fourth leak prevention valve are located at a distance from a respective end of the FDL within a range of 1-2 inches.

8. The TTM system of claim 1, wherein the first leak prevention valve and the second leak prevention valve are check valves.

9. The TTM system of claim 8, wherein the first leak prevention valve and the second leak prevention valve are duckbill valves.

10. A targeted temperature management (TTM) system, comprising:

a TTM module configured to provide a TTM fluid;

a fluid delivery line (FDL) including a FDL hub, a fluid delivery lumen and a fluid return lumen; and a pad configured to facilitate thermal energy transfer between the TTM fluid and a patient, the pad comprising:

a pad portion configured for placement on the patient including a first connection point including a first leak prevention valve and a second connection point including a second leak prevention valve, a fluid delivery conduit extending away from the pad portion, the fluid delivery conduit including a delivery conduit connector at a proximal end thereof and configured to couple with the first connection point, and a fluid return conduit extending away from the pad portion, the fluid return conduit including a return conduit connector at a proximal end thereof and configured to couple with the second connection point.

11. The TTM system of claim 10, wherein the pad further comprises a connector coupled to a distal end of each of the fluid delivery conduit and the fluid return conduit.

12. The TTM system of claim 10, wherein the first leak prevention valve is configured to enable the TTM fluid to flow into the pad portion while preventing flow out of the pad portion, and wherein the second leak prevention valve is configured to enable the TTM fluid to flow out of the pad portion while preventing flow into the pad portion.

13. The TTM system of claim 10, wherein the first leak prevention valve and the second leak prevention valve are located at a distance from an opening of a respective connection point within a range of 1-2 inches.

14. The TTM system of claim 10, wherein the first leak prevention valve and the second leak prevention valve are check valves.

15. The TTM system of claim 14, wherein the first leak prevention valve and the second leak prevention valve are duckbill valves.

* * * * *